(12) United States Patent  
Hamilton et al.

(10) Patent No.: US 7,998,149 B2
(45) Date of Patent: Aug. 16, 2011

(54) SUTURING DEVICE, SYSTEM, AND METHOD

(75) Inventors: Henry H. Hamilton, Hillsborough, CA (US); Yuri Belman, Mountain View, CA (US); Alexander Borisovich Zatyuryukin, Moscow (RU); Patricia A. Moore, Incline Village, NV (US)

(73) Assignee: Suturenetics, Inc., Incline Village, NV (US)

( * ) Notice: Subject to any disclaimer, the term of this patent is extended or adjusted under 35 U.S.C. 154(b) by 1223 days.

(21) Appl. No.: 11/532,032

(22) Filed: Sep. 14, 2006

(65) Prior Publication Data
US 2007/0060931 A1 Mar. 15, 2007

Related U.S. Application Data

(63) Continuation-in-part of application No. 11/227,981, filed on Sep. 14, 2005, now Pat. No. 7,588,583.

(51) Int. Cl.
*A61B 17/04* (2006.01)
(52) U.S. Cl. ........................ 606/144; 606/139
(58) Field of Classification Search .................. 606/139, 606/144–148
See application file for complete search history.

(56) References Cited

U.S. PATENT DOCUMENTS

| | | |
|---|---|---|
| 3,827,277 A | 8/1974 | Weston |
| 3,946,740 A | 3/1976 | Bassett |
| 4,242,902 A | 1/1981 | Green |
| 4,373,530 A | 2/1983 | Kilejian |
| 4,440,171 A | 4/1984 | Nomoto et al. |
| 5,282,800 A * | 2/1994 | Foshee et al. .................. 606/52 |
| 5,336,230 A | 8/1994 | Leichtling et al. |
| 5,665,096 A | 9/1997 | Yoon |
| 5,749,879 A | 5/1998 | Middleman et al. |
| 5,897,563 A | 4/1999 | Yoon et al. |

(Continued)

FOREIGN PATENT DOCUMENTS
EP 1 862 125 12/2007
(Continued)

OTHER PUBLICATIONS

"Quik-Stitch® Endoscopic Suturing System" http://paresurgical.com.com [downloaded from Internet Apr. 10, 2008] 1 page total.

(Continued)

*Primary Examiner* — Darwin P Erezo
(74) *Attorney, Agent, or Firm* — Kilpatrick Townsend and Stockton LLP

(57) ABSTRACT

Improved medical suturing devices, systems, and methods may hold a suture needle at a fixed location relative to a handle of the device, allowing the surgeon to grasp and manipulate the handle of the suturing device to insert the needle through tissues in a manner analogous to use of a standard needle gripper. Cycling the handle from a closed position to an open position and back to the closed position may alternate the device between gripping the needle with a first clamp (for example, along a proximal portion of the needle) to gripping the needle with a second clamp (for example, along a distal portion of the needle) and optionally back to gripping with the first clamp, with the needle often staying at a substantially fixed location relative to the suturing device body. Related single-clamp needle grasping devices can be bent plastically by a surgeon, and/or have bodies that are grasped by a hand while a portion of the hand actuates a handle.

22 Claims, 23 Drawing Sheets

U.S. PATENT DOCUMENTS

| | | | |
|---|---|---|---|
| 5,908,429 | A | 6/1999 | Yoon |
| 5,938,668 | A | 8/1999 | Scirica et al. |
| 5,954,733 | A | 9/1999 | Yoon |
| 5,984,932 | A | 11/1999 | Yoon |
| 5,993,466 | A | 11/1999 | Yoon |
| 5,993,467 | A | 11/1999 | Yoon |
| 6,004,332 | A | 12/1999 | Yoon et al. |
| 6,071,289 | A | 6/2000 | Stefanchik et al. |
| 6,086,601 | A | 7/2000 | Yoon |
| 6,126,665 | A | 10/2000 | Yoon |
| 6,159,224 | A | 12/2000 | Yoon |
| 6,206,894 | B1 | 3/2001 | Thompson et al. |
| 6,638,286 | B1 | 10/2003 | Burbank et al. |
| 7,001,400 | B1 | 2/2006 | Modesitt et al. |
| 7,185,597 | B1 | 3/2007 | Phillips et al. |
| 7,338,504 | B2 | 3/2008 | Gibbens, III et al. |
| 7,588,583 | B2 * | 9/2009 | Hamilton et al. ............. 606/144 |
| 2006/0079914 | A1 | 4/2006 | Modesitt et al. |
| 2006/0142785 | A1 | 6/2006 | Modesitt et al. |
| 2006/0173469 | A1 | 8/2006 | Klein et al. |
| 2006/0190035 | A1 | 8/2006 | Hushka et al. |
| 2006/0212048 | A1 | 9/2006 | Crainich |
| 2007/0060931 | A1 | 3/2007 | Hamilton et al. |
| 2007/0167959 | A1 | 7/2007 | Modesitt et al. |
| 2007/0179509 | A1 | 8/2007 | Nagata et al. |

FOREIGN PATENT DOCUMENTS

| | | |
|---|---|---|
| WO | WO 2006/012128 A2 | 2/2006 |
| WO | WO 2006/023348 A1 | 3/2006 |
| WO | WO 2006/125835 A1 | 11/2006 |
| WO | WO 2007/033314 A2 | 3/2007 |
| WO | WO 2007/037326 A1 | 4/2007 |
| WO | WO 2007/089603 A2 | 8/2007 |
| WO | WO 2007/129121 A1 | 11/2007 |
| WO | WO 2007/135629 A1 | 11/2007 |

OTHER PUBLICATIONS

"The Running Device™—Surgery's Best Suturing Technology™" http://www.lsisolutions.com/home.html [downloaded from Internet Apr. 10, 2008] 1 page total.

"Autosuture—Advancing Possibilities in Surgery™" http://www.autosuture.com/autosuture/ [downloaded from Internet Apr. 10, 2008] 1 page total.

"Endo Stitch™ 10 mm Suturing Device Instructions for Use and product description," 4 pages downloaded from internet May 20, 2005, by United States Surgical, a division of Tyco Healthcare Group LP (2005).

"Fastclose™ Device, Instructions for use," product brochure, 2 pages published by SuturTek, Inc. (2001).

"SuturTek—SuturTek Products—FastClose™ Device," product brochure, 2 pages downloaded from internet May 20, 2005, by SuturTek, Inc. (2001).

"SuturTek—SuturTek Products—The Technology," product brochure, 1 page downloaded from internet May 20, 2005, by SuturTek™, Inc. (2001).

"SuturTek—SuturTek Products—FastClose In Use," product brochure, 1 page downloaded from internet May 20, 2005, by SuturTek™, Inc. (2001).

"Home Page for Auto Suture," product brochure, 1 page downloaded from internet May 20, 2005, by United States Surgical, a division of Tyco Healthcare Group LP (2005).

International Search Report and Written Opinion of PCT Application No. PCT/US06/35804, dated Jul. 11, 2008, 8 pages total.

* cited by examiner

SUTURING DEVICE, SYSTEM, AND METHOD

CROSS-REFERENCE TO RELATED APPLICATION

This is a continuation-in-part patent application which claims priority from U.S. patent application Ser. No. 11/227,981 filed Sep. 14, 2005, now U.S. Pat. No. 7,588,583, the full disclosure of which is incorporated herein by reference.

BACKGROUND OF THE INVENTION

The present invention generally relates to medical devices, systems, and methods. In specific embodiments, the invention provides devices, systems, and methods for suturing tissues in open surgery, minimally invasive surgical procedures, and the like.

Although many aspects of surgery have changed radically over the last several decades, some surgical techniques have remained remarkably constant. For example, as was true fifty years ago, suturing remains a common technique for approximation of tissues, ligation of tissues, affixing tissues together, and the like.

Suture has been used in open surgical procedures for generations to therapeutically treat diseased tissue and to close surgical access sites and other wounds. More recently, the use of minimally invasive surgical techniques has expanded, with surgical therapies often being performed at internal surgical sites. Although a wide variety of visualization techniques (including laparoscopes and other endoscopic viewing devices, fluoroscopy and other remote imaging modalities, and the like) have been developed to allow surgeons to view these internal surgical sites, and although a large variety of new tissue treatment techniques have been developed (including ultrasound techniques, electrosurgical techniques, cryosurgical techniques, and the like) and are now widely available, many modern surgical interventions continue to rely on suturing.

A wide variety of alternatives to suturing of tissues have been developed, and have gained varying degrees of acceptance in certain surgical procedures. Staples and tissue adhesives are used quite frequently in many open and minimally invasive surgical settings, and a variety of tissue welding techniques have also been proposed. Nonetheless, suturing remains ubiquitous in surgery, as suturing provides a number of advantages over many of the alternatives.

Suture's advantages include the large knowledge and skill base that surgeons have developed over the years. Additionally, a variety of off-the-shelf, pre-packaged surgical needles with suture are available from a large number of suppliers at very reasonable cost. Surgeons are able to precisely control the location of suture stitches by grasping the suture needle and first pushing it and then pulling it through the target tissue. In open surgery the surgeon may manually grasp the suture needle directly with his or her hand, although both open and minimally invasive procedures are often performed by grasping the needle with a needle grasping tool and manipulating the tool to place the suture stitches. The results obtained using suture are highly predictable, although dependent on the skill of the surgeon. In light of its advantages, the use of suture does not appear likely to disappear any time soon, with even modern robotic surgical techniques often making use of suture.

Although suture remains popular in surgery at least in part due to its significant advantages, suturing is not without disadvantages. In particular, placing a large number of suture stitches can be tiring and quite time-consuming. Manipulation of a suture needle can be difficult even in open surgery due to the limited space that is often available around the target tissues. The challenges of manipulating suture needles may be even greater in minimally invasive surgical procedures, where the needles are often manipulated using long-handled tools extending through a small aperture, typically while viewing the procedure on a display which is offset from the surgical site. Tying knots with a desired amount of tension and the like may call for intricate and precise manipulation of the suture, further complicating and delaying open and minimally-invasive surgeries. In fact, the time spent closing/suturing the access site may be significantly greater than the time spent treating the underlying target tissues for many procedures.

There have been a variety of proposals for modifications to standard surgical suturing structures and methods to try to address the above disadvantages. At least some of these proposals may seek to rely on specialized and/or proprietary suturing needle systems, which could increase costs and preclude their wide acceptance, especially in third world countries. Unfortunately, many proposals for modifying existing suturing techniques may also decrease the surgeon's control over the placement of the suture, such as by relying on an automated or indirect mechanical movement of a device to drive a suture needle into and/or through tissues. While these new proposals have in the past or may in the future gain varying degrees of acceptance in one or more surgical procedures, standard suturing techniques continue to predominate throughout surgery in general.

In light of the above, it would be desirable to provide improved suturing devices, systems, and methods. It would be generally desirable to maintain some, most, or all of the advantages of standard suturing techniques, preferably while decreasing the time required for suturing, the strain on the surgeon, the training involved in achieving competence or time-efficiency in suturing techniques, or the like. It would be particularly advantageous if these improvements could be provided without requiring extensive capital investments for new equipment, without significant increases in complexity of the suturing process, or without having to resort to specialized or proprietary suturing needles and the like. Alternative needle grasper structures which increased the ease and accuracy of stitching, and/or which are readily adapted for a variety of different procedures and patient physiologies would also be desirable.

BRIEF SUMMARY OF THE INVENTION

The present invention generally provides improved medical suturing devices, systems, and methods. Embodiments of the invention provide improved suturing devices and methods that maintain some or all of the advantages of standard open and/or minimally invasive suturing techniques while providing enhanced speed and ease of use. Exemplary suturing devices may hold a suture needle at a fixed location relative to a handle of the device, allowing the surgeon to grasp and manipulate the handle so as to insert the needle through the tissues to be sutured in a manner closely analogous to use of a standard needle gripper. Cycling of the handle of the device from a closed position to an open position and back to the closed position may result in the needle being alternatingly gripped by a first clamp (for example, along a proximal portion of the needle, suitable for insertion of the tip of the needle into and through tissue), and then by a second clamp (for example, along a distal portion of the needle, suitable for pulling the protruding needle out from the tissue), and optionally again by the first clamp (ready for initiation of the next stitch). The needle will often remain at a substantially fixed location relative to the body and handle of the suturing device during at least the insertion and/or pulling of the needle through the tissue, allowing the surgeon to maintain precise control over needle movement and positioning of the suture. Advantageously, standard off-the-shelf suturing needles with their attached suture may be used, and the device may be employed in an open surgical setting or a minimally invasive procedure. Needle grasping devices and methods are also provided which can be bent plastically by a surgeon for use in a particular patient, and/or having advantageous ergonomics for use in surgery, these needle graspers optionally having only a single clamp for grasping of an associated needle.

In a first aspect, the invention provides a suturing method. The suturing method comprises inserting a distal portion of a suturing needle distally through a tissue by moving a body of a suturing device. The body is moved while a clamp of the suturing device holds the needle at a fixed location relative to the body. The distal portion of the needle is grasped with a second clamp of the suturing device, and the proximal portion of the needle is released from the first clamp. The proximal portion of the needle is pulled through the tissue by moving the body while the second clamp holds the needle.

The second clamp will often hold the needle at a fixed location relative to the body of the suturing device while the needle is pulled free. The needle may also remain at a substantially fixed location relative to the body of the suturing device while alternating the clamps, for example, by grasping the proximal portion of the needle with the first clamp and only then releasing the distal portion of the needle from the second clamp. The inserting of the distal portion of the needle into the tissue with the first clamp, switching clamps, and then pulling the proximal portion of the needle through the tissue with the second clamps can significantly facilitate forming a plurality of suture stitches, and may avoid completely releasing the needle and/or re-aligning the needle with the device each time a stitch is formed. Handing the needle back and forth between the first and second clamps will often be effected by actuating a handle of the suturing device with a hand of a surgeon, the handle typically moving from an open handed configuration to a closed grasp configuration. Preferably, the handle will be in the closed grasp configuration at least while inserting the distal portion of the needle into tissues.

In the exemplary embodiments, cycling the handle (for example, from closed to open, and back to closed) alternates which clamp of the suturing device is supporting the needle from the first clamp, to the second clamp, and back (optionally) to the first clamp. By having both clamps supporting the needle for at least a portion of the handle actuation cycle, unintended movement of the needle relative to the body of the device (and the handle) can be inhibited.

The suturing device body will often include a housing containing a linkage, and the linkage may include an alternatable drive element. The linkage will often drivingly couple the handle to the first and second clamps. With each handle actuation cycle, the alternatable drive element may move back an forth between a first configuration and a second configuration. In its first configuration, the alternatable drive element may drive a first portion of the linkage coupled to the first clamp. In its second configuration the alternatable drive element may drive a second portion of the linkage coupled to the second clamp.

In an exemplary embodiment, the handle actuation cycle may effect rotation of a drive wheel. The first and second linkage portions may each comprise a driven wheel, and the alternatable drive element in the first configuration may drivingly couple the drive wheel with the driven wheel of the first linkage portion. In the second configuration of the alternatable drive element, it may drivingly couple the drive wheel with a driven wheel of the second linkage portion. The alternatable drive element may be, for example, slidingly or pivotally attached to the drive wheel and may move back and forth so as to engage surfaces of the driven wheels on either side of the drive wheel, with the wheels being driven about a common axis. Other linkage embodiments may employ an alternatable drive element in the form of a slider having alternative positions during axial movement, or the like. Still further alternative linkage embodiments may employ rack and pinion gears and cams, cables, and/or the like, with or without alternatable drive elements.

In many embodiments, the first clamp will be displaced laterally from around an axis of the needle when the second clamp is used to move the needle through tissue. Similarly, the second clamp may be displaced laterally from around the needle when the first clamp is used to move the needle through tissue. Each clamp may, for example, be mounted to an associated shaft, and these shafts may reciprocate so as to extend distally from a housing of the body before closing of the clamp around the needle. In some embodiments, the clamp may also pivot about an axis of the shaft while moving between a retraced position and an extended needle grasping position. A spring or other biasing means may inhibit closing of the clamp before the clamp is properly disposed around the needle, or the linkage may otherwise be configured to extend the shaft before closing of the clamp. In some embodiments, the shafts, clamps, and needle may move axially slightly relative to the housing of the body when the handle is cycled.

Conveniently, a release input may be provided on the suturing device so as to release the needle from both the first and second clamps. The needle may comprise an off-the-shelf needle which is sold primarily for standard open or laparoscopic procedures. These needles often come prepackaged with suture, and are available in a large variety of needle sizes and configuration, suture types (including resorbable and non-resorbable sutures), and the like, often at very modest costs. Alternatively, specialized needles may also be employed. An alternatable latch may optionally maintain either of the clamps closed over the needle during needle manipulation. The body and handle may be configured so that a rigid portion of the body can be comfortably grasped by the hand while a portion of the hand (such as the fingers) articulates the handle, so that inadvertent movement of the body and needle relative to the hand is inhibited. The surgeon may optionally plastically bend a distal extension of the body along its longitudinal axis for use with a particular patient physiology. In such embodiments, drive components within the body will typically be sufficiently flexible to allow operation of the clamps through the bent body In another aspect, the invention provides a suturing device for use with a suture needle. The device comprises a body having a proximal end and a distal end. A first clamp is disposed near the distal end of the body. A second clamp is also disposed near the distal end of the body. A linkage effects movement of the first and second clamps between a grasping configuration and a displaced configuration. Each clamp grasps the needle at an associated grasping location in the grasping configuration, and is laterally displaced from the needle in the displaced configuration. The grasping locations are substantially fixed relative to the body.

In another aspect, the invention provides a suturing device for use with a suturing needle. The device comprises a body having a proximal end and a distal end. A handle is disposed near the proximal end of the body. The handle is actuatable from a first configuration to a second configuration and back to the first configuration so as to define an actuation cycle. A first clamp and a second clamp are disposed near the distal end of the body, and the clamps are coupled to the handle so that an actuation cycle initiated while the first clamp is grasping the needle results in grasping of the needle with the second clamp and release of the needle from the first clamp, and (optionally) then in the first clamp grasping the needle and the needle being released from the second clamp.

In yet another aspect, the invention provides a suturing device for use with a suturing needle. The suturing device comprises a body having a proximal end and a distal end, with a clamp extendable distally of the body. Biasing means is coupled to the clamp to urge the clamps closed sufficiently to grasp the needle therein for suturing with the needle. An articulatable handle is disposed near the proximal end of the body, and a linkage couples the handle to the clamp so that manual articulation of the handle opens the clamp to release the needle. Such suturing devices may optionally have only a single needle-grasping clamp.

In yet another aspect, the invention provides a suturing device for use with a suturing needle. The suturing device comprises a rigid body having a proximal end and a distal end, and a clamp extendable distally of the body. An articulatable handle near the proximal end of the body is configured for manipulation by fingers of a hand while the hand engages the body near the proximal end. A linkage coupling the handle to the clamp so that manual articulation of the handle by the fingers effects opening and closing of the clamp to grasp and release the needle. Only a single clamp may be provided, or a plurality of clamps, with the device ideally enhancing control over movement of the needle by the hand by inhibiting movement of the needle relative to the hand during opening and closing of the clamp.

In yet another aspect, the invention provides a method for securing suture using a needle driver. The method comprises placing a suture through a tissue by grasping a proximal end of a needle with the needle driver and inserting the needle into the tissue at a first insertion point. The needle is inserted with the needle driver so that a distal end of the needle protrudes from the tissue at a first exit point. The distal end of the needle is grasped by the needle driver and pulled distally from the tissue, with the suture being coupled to the needle. A first suture loop is formed in the tissue by, after the suture has been placed through the tissue, again supporting the proximal end of the needle with the needle driver, inserting the needle into the tissue at a second insertion point and removing the needle from a second exit point in a manner similar to that used to first place the suture through the tissue. A second loop is formed in a similar manner, resulting in a third insertion point and a third exit point, and a third loop is also formed. The third loop extends across at least one (and preferably both) of the first and second loops between a third exit point and the fourth insertion point so as to define crossed loops in the suture. The needle is pulled from the fourth exit point sufficiently that the crossed loops secure the suture to the tissue. Advantageously, this knot may be formed without releasing the needle driver from the hand of the surgeon. The needle grasping and driving devices described herein are particularly advantageous for use in this method.

DETAILED DESCRIPTION OF THE INVENTION

Figure 1:
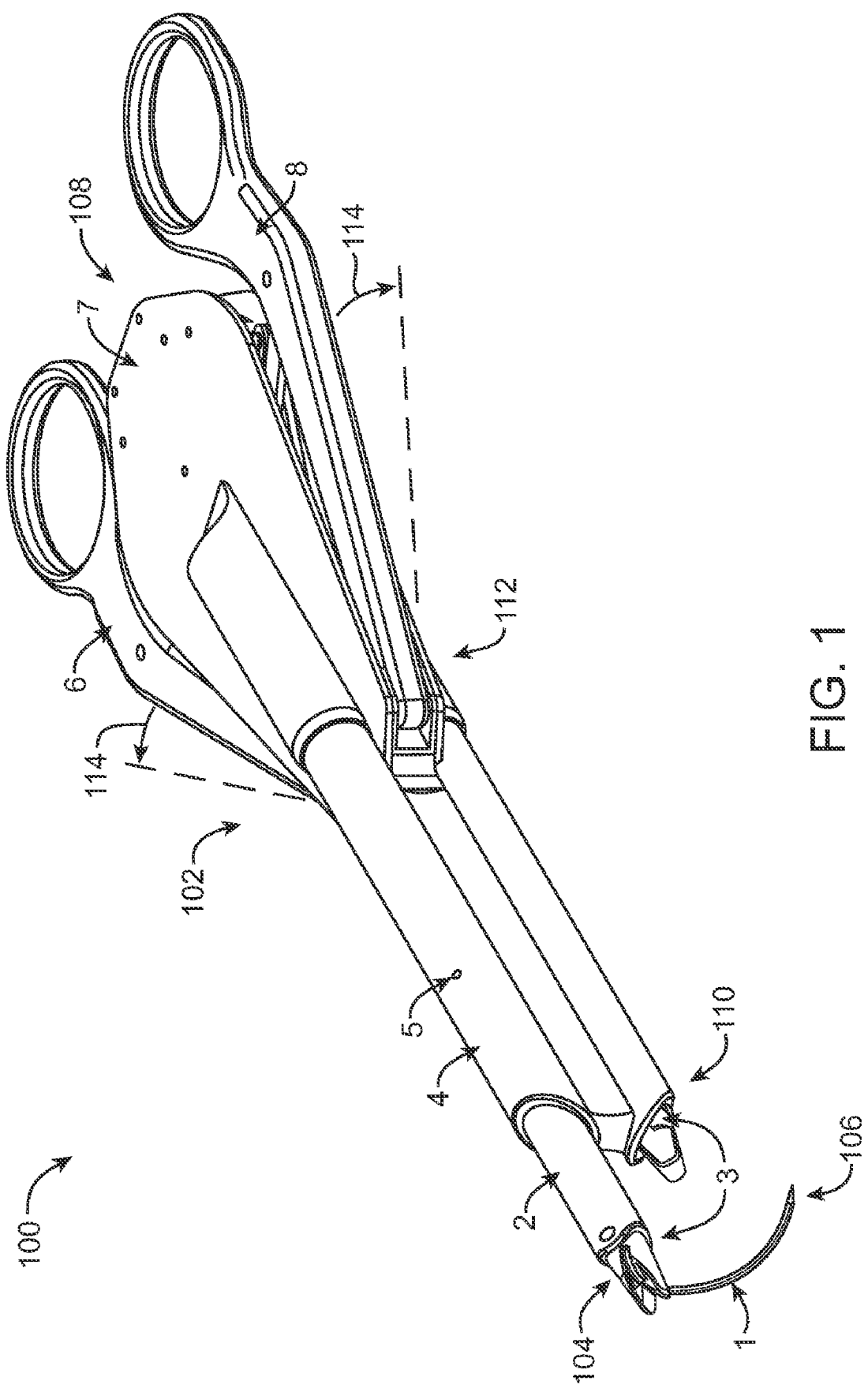
FIG. 1 is a perspective view of an exemplary embodiment of a suturing device with one of the clamps of the suturing device grasping a suturing needle.

The present invention is generally directed to improved medical suturing devices, systems, and methods. Exemplary embodiments of the invention provide improved suturing devices and methods for suturing tissues that can significantly increase the speed and ease of suturing, particularly when suturing of long incisions or where large numbers of stitches are to be deployed.

The invention should find a wide variety of applications for stitching anatomical tissues in both humans and animals. Along with endoscopic operations (for example, in laparoscopy) these structures and methods may find use in other areas of surgery where tissues are to be stitched, providing particular advantages for stitching of large incisions by increasing the ease and speed with which each individual stitch may be placed, as well as facilitating and expediting the formation of knots in the suture. The suturing devices and associated methods described herein may, for example, be used suture a wide variety of strata of anatomical tissues, including (but not limited to) subcutaneous layers, fascia, the outer skin, various organs (including the uterus), and the like. While exemplary embodiments are set forth below, these suturing devices and methods may be applicable to a wide variety of suturing operations, including open surgery, large and small cavity procedures, endoscopic procedures, microsurgeries (including for suturing of veins, arteries, and the like), and many specialized surgeries. Embodiments of these devices and methods may be particularly useful for surgeries involving long incisions, including plastic surgeries. A wide variety of blood vessels, including both veins and arteries, may also be stitched using the techniques described herein, for formation of anastomoses and the like. Along with increasing the speed and/or ease of forming surgical suture stitches, embodiments of the invention will often maintain the control a doctor has over the placement of the sutures by maintaining a fixed relationship between the movements of the doctor's hand and the insertion and withdrawal of the suturing needle. Hence, among the procedures which may benefit from the invention are subcuticular peritoneum, fascia closure, and skin closure.

While embodiments of the invention may include (or be used within) a powered or automated system, optionally making use of electromechanical power, hydraulic power, or the like (for example, with some embodiments being included within a robotic system), other embodiments may be configured for manual manipulation by one or more hands of a surgeon, often without having to resort to complex subsystems or external power.

Many embodiments of the devices described herein will be sterilizable so as to allow repeated use. Sterilization may be effected using autoclave techniques, chemical sterilization, irradiation, or the like, with most or all of the structures of the suturing device being formed of materials suitable for repeated sterilization (such as stainless steel, other metals and alloys, and the like). In general, the suturing device may comprise one or more plastics and/or metals common to surgical devices. Although specialized or proprietary suturing needles may be employed in some embodiments (for example, needles having flat gripping surfaces so as to maintain an alignment between the needle and an associated clamp), many embodiments of the suturing device will be suitable for use with standard off-the-shelf suture needles such as those packaged with any of a wide variety of permanent or resorbable suture materials in a hermetically sealed package. In fact, the invention may find some of its most immediate applications for facilitating surgical procedures performed manually in Third World countries, allowing physicians to treat a larger number of patients with greater ease than can be done using standard suturing techniques, but without the cost or complexity of recently-proposed automated suturing systems.

Referring now to FIG. 1, an exemplary suturing system 100 generally includes a suturing device 102 and a needle 1. Needle 1 generally has a proximal end 104 and a distal end 106, with at least the distal end being sharpened to facilitate insertion of the needle distally into and through tissues. Surgical needles are often formed with a curving shape between the proximal and distal ends, and are often packaged with a suture extending from proximal end 104, with the needle sometimes being referred to as an acus.

Suturing device 102 generally has a body 112 having a proximal end 108 and a distal end 110. A pair of clamps 3 are disposed near the distal end 110, while first and second handles 6, 8 are disposed near proximal end 108. Body 112 may include a proximal housing 7 and a distal extension 4. The distal extension may have a pair of channels, with each channel reciprocatably receiving a shaft 2 supporting an associated clamp 3.

In this embodiment, clamps 3 are mirror-symmetric, although they may alternatively have differing shapes. Clamps 3 are generally offset so as to grip axially offset portions of needle 1, with one of the clamps gripping a more proximal portion of the needle and the other clamp gripping a more distal portion of the needle. When handles 6, 8 are in a close-handed configuration as illustrated in FIG. 1, only one of clamps 3 will typically grip needle 1, the other clamp being retracted proximally away from the needle. Handles 6, 8 have openings for receiving fingers of the surgeon's hand, and the surgeon will typically actuate the handles by opening them from the closed-handed configuration shown to an open-handed configuration 114. Starting with handles 6, 8 in the closed (as shown in FIG. 1), when the handle is moved to open-handed configuration 114 and is then returned to the closed-handed configuration, the handle may be described as having completed an actuation cycle.

With each actuation cycle of handles 6, 8, the clamp 3 supporting needle 1 is alternated so that a needle initially supported by grasping the needle in first clamp along a proximal portion of the needle will, when handles 6, 8 are in open-handed configuration 114, instead be supported by the second clamp along a more distal portion of the needle. As handles 6,8 move back to the closed-handed configuration to complete the cycle, the clamps again alternate, so that closing of the handle results in extension of the proximal clamp, gripping of needle 1 with that proximal clamp, release of the needle from the distal clamp, and retraction of the distal clamp. The position of needle 1 relative to body 112 may remain substantially fixed throughout the handle actuation cycle, although the shafts may move axially slightly as the needle goes from being held by one clamp, to both clamps, and then to the other clamp, with this movement of the needle being less than a length of the needle.

Figure 2:
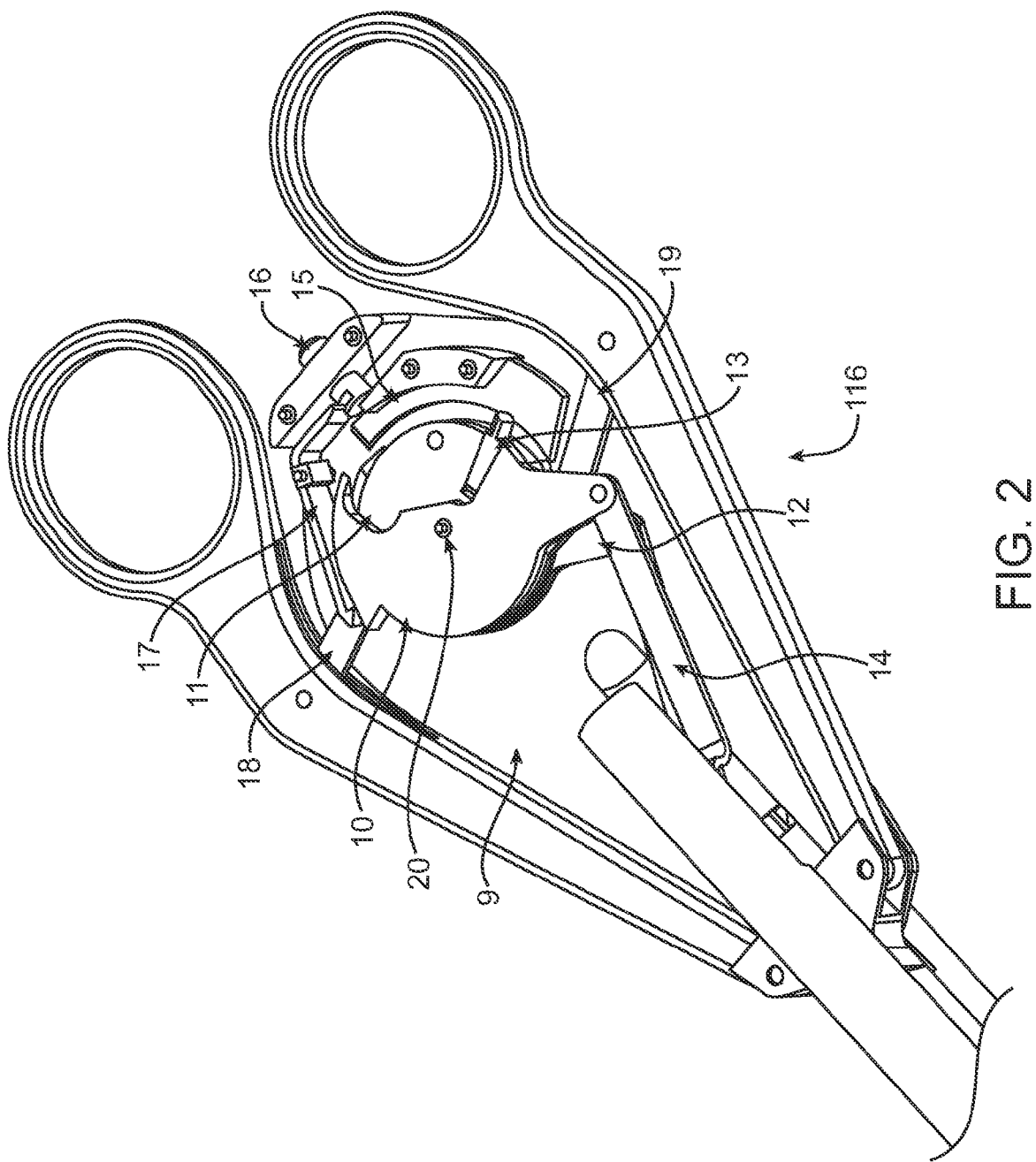
FIG. 2 is a perspective view of a proximal portion of the suturing device of FIG. 1, with a cover removed from a proximal housing of the suturing device to show a portion of a linkage coupling a handle of the suturing device to the clamps of the suturing device.

Referring now to FIGS. 1 and 2, handles 6, 8 are pivotally attached to housing 7 of body 112. Housing 7 generally includes at least one lid 9 (the top lid shown removed in FIG. 2), with the proximal housing preferably including opposed first and second lids 9 on opposed major surfaces of the body. Lids 9 and the other structures of housing 7 generally enclose a drive linkage 116 coupling handles 6, 8 to clamps 3. In the embodiment of FIGS. 1-9, drive linkage 116 generally includes a drive wheel 11 and two driven wheels 10 and 12. The driven wheels 10 and 12 are mirror-symmetric and joined by tie rods 14 and 21 to clamps 3.

Figure 3:
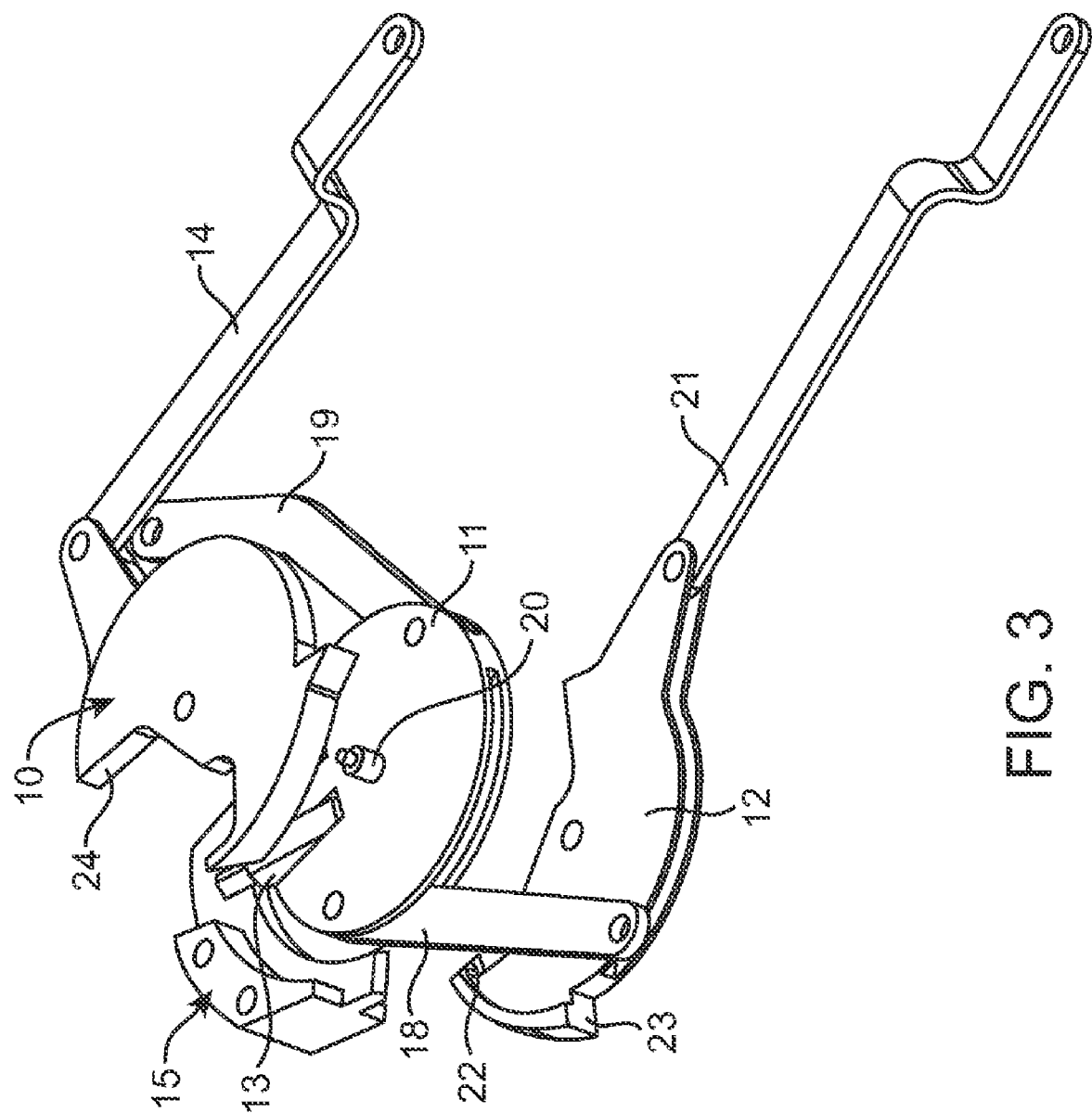
FIG. 3 is an exploded perspective view of components of the linkage shown in FIG. 2.
Figure 4:
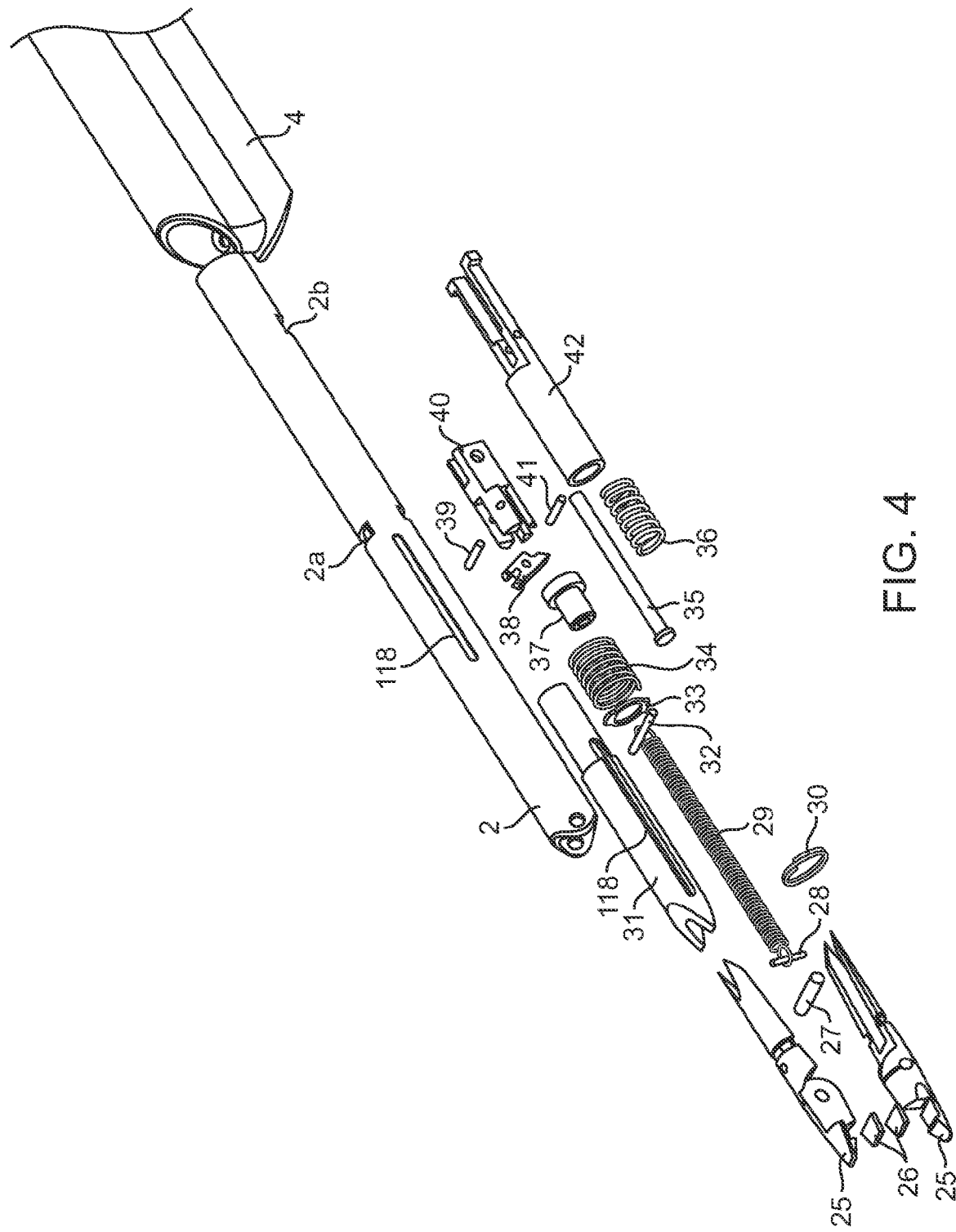
FIG. 4 is an exploded view of a distal portion of the suturing device of FIG. 1, showing components of a clamp along with a reciprocatable shaft and elements of the linkage that effect movement of the reciprocatable shaft and actuation of the clamp.

Referring now to FIGS. 1-3, driven wheel 10 has a thrust surface 24, while driven wheel 12 has a stop surface 23 and an incline 22. The driving wheel is supported so as to rotate about an axle 20, the driving wheel also having a lug 13. The driving wheel 11 is coupled to handles 6, 8 by ties 18 and 19, so that actuation of the handles relative to the body 7 induces rotation of driving wheel 11 about the axle. The driven wheels 10, 12 rotate coaxially with driven wheel 11.

Lug 13 generally comprises an alternatable configuration driving element. Lug 13 either drivingly couples driving wheel 11 with driven wheel 10, or with driven wheel 12, depending on the configuration of lug 13 at the time. More specifically, when lug 13 is disposed above a guide 15 as shown in FIG. 2, the lug drivingly couples the driving wheel 11 with the upper driven wheel 10. When lug 13 is disposed below guide 15, the lug drivingly engages driven wheel 12, and is disengaged from driven wheel 10. A reset or release input button 16 interacts with guide 15 and a spring-loaded positioning arm 17 so as to allow both clamps 3 to release needle 1.

As can be understood with reference to FIGS. 1-4, each clamp 3 is connected by an associated shaft 2 to the remaining components of drive linkage 116. Shafts 2 each include a lengthwise slot 118 (see FIG. 4), which allows the shaft to move within the channels of body extension 4. Guiding pins 32 ride in slots 118, and the guiding pins 32 are also fixed in extensions 4 within openings 5.

Moving wedges 31 within shafts 2 also have lengthwise slots 118 for receiving guiding pins 32. The wedge surfaces of moving wedges 32 engage corresponding surfaces of working jaws 25, with the working jaws forming the open and closable structure of clamps 3. More specifically, distal movement of moving wedge 31 against a corresponding surface of working jaws 25 closes clamps 3, the working jaws being attached to a distal clevis of shaft 2 by axle 27. A spring ring 30 biases working jaws 25 to an open configuration, allowing them to move around and capture needle 1 before the working jaws are forced shut by the moving wedges.

Working jaws 25 may have a variety of surfaces for holding needle 1, the clamps preferably holding the needle so that movement of the needle relative to suturing device 100 is inhibited during stitching. The surfaces of working jaws 25 may be hardened by deposition of diamond or a diamond-like carbon, or inserts 26 of a material harder than that of working jaws 25 may be provided. Optionally, working jaws 25 may have hard-surfaced inserts comprising tungsten and/or cobalt, with the inserts optionally being fabricated using powder sintering or the like.

A return spring 28 extends between pin 28 in working jaws 25 and the guiding pin 32, with the return spring partially fixed within a lumen of moving wedge 31. A spring 34 in the proximal portion of moving wedge 31 is held by a plug 37, with the distal end of spring 34 interacting with shaft 2 via thrust ring 33. Spring 34 can bring the moving wedge 31 into a position suitable for releasing the working jaws. A compensation spring 36 pressed against plug 37 writes on a rod 35 of a pusher 42 so as to maintain a desired axial force. Pusher 42 has an insert 40, which is connected with the pusher 42 by pin 39 and lug 38. The lug rotates about axle 41.

When handles 6 and 8 are moved apart to an open-handed configuration 114, a retracted clamp 3 and its associated shaft 2 moves from within a channel of body extension 4. While retracted, the moving wedge 31 is biased by spring 34 away from working jaws 25, so that spring ring 30 is free to open the clamp to allow it to extend around needle 1. Extension of compensating spring 34 may be at its greatest point while the associated clamp 3 is retracted, and insert 40 extends from pusher 42 with lug 38 in the insert.

As handles 6 and 8 are brought together, driving wheel 11 is turned by connector ties 18, 19. Lug 38 interacts with thrust surface 24 of driven wheel 10 and moves the driven wheel 10 in rotation. The motion of driven wheel 10 is transferred by tie rod 14 so as to move insert 40 axially along body extension 4. The insert, in turn, moves the pusher 42 along body extension 4, the relative position of the insert 40 and pusher 42 being maintained by an inner surface of shaft 2 interacting with plug 30 so as to inhibit rotation of the plug about axle 41. Pusher 42 presses spring 34 and compensation spring 32, and via plug 37 and thrust ring 33, moves shaft 2. The movement of shaft 2 overcomes spring 29 and extends the shaft from the channel of body extension 4.

During distal movement of pusher 42, spring 34 and compensating spring 36 are sufficiently stiff so as to inhibit elongation, as their spring coefficients are significantly higher than that of return spring 29. However, engagement between an end of slot 118 in shaft 2 and guiding pin 32 eventually inhibits further distal movement of the shaft.

Once shaft 2 has stopped its distal movement (due to engagement of lengthwise slot 118 with guiding pin 32), spring 34 begins to contract, its rigidity being lower than that of compensating spring 26. As a result, moving wedge 31 begins to extend distally relative to working jaws 25, the corresponding surfaces of the wedge and working jaws sliding against each other so as to move the proximal ends of the working jaws apart and bringing the distal needle gripping inserts 26 of working jaws 25 together so as to grasp needle 1. As spring 34 contracts, contraction of compensation spring 36 also begins and the insert 40 moves. When lug 38 extends into and/or engages window 2a of shaft 2, pusher 42 engages a surface of body extension 4 or proximal housing 7, and axial movement of the pusher stops. Insert 40 continues moving, so that lug 38 rotates around axle 41. The lug interacts with an edge of shaft 2 and, overcoming compensation spring 36, starts to draw shaft 2 and its contents into body extension 4.

The clamping force on needle 1 by clamps 3 may be determined by the spring characteristics of compensating spring 36 so as to remain within a desired range. Advantageously, the clamping force imposed by suturing device 100 on needle 1 may correspond to forces applied by standard needle holders. Thrust surface 23 of driven wheel 12 approaches a tooth of spring-loaded fixing arm 17, and overcoming the spring, the thrust surface passes under the tooth, releasing the tooth so that the tooth and thrust surface are positioned for neutral engagement. After the thrust surface 23 of the driven wheel 12 passes beyond the tooth of spring loaded fixing arm 17, engagement of the thrust surface and tooth inhibit the return of the driving linkage 116 to its prior configuration, thereby inhibiting the release of needle 1 from the closed working jaws 25 so that the needle is not dropped.

As handles 6, 8 continue to move toward the open-handed configuration of the handle actuation cycle, movement of driven wheel 12 is inhibited by spring-loaded fixing arm 17. Driving wheel 11 nonetheless turns, and is reset. More specifically, incline 22 of driven wheel 12 moves lug 13 from a configuration above guide 15 to a configuration in which the lug is disposed under the guide. Hence, when handles 6, 8 continue to move, here towards a closed-handed configuration, the lug 13 will interact with thrust surface 24 of the driven wheel 10. The description above regarding driven wheel 12 is thus repeated but with driven wheel 10 instead. When moving under the spring-loaded fixing arm 17, the thrust surface 23 of driven wheel 12 lifts the spring-loaded fixing arm 17 and releases driven wheel 10.

By action of spring 34, moving wedge 31 is retracted proximally from between the proximal ends of working jaws 25, so that the proximal ends of the working jaws are brought together by spring-loaded ring 30. Distal ends of working jaws 25 thereby move apart and the needle is released.

Each repeated opening and closing actuating cycle of handles 6, 8 alternates the needle between being held by one, and then the other of clamps 3, and often back to the first clamp. In other embodiments, each handle actuation cycle effects transfer of the needle from one clamp to the other, with the needle returning to be held solely by the first clamp only with a second handle actuation cycle. Regardless, during each cycle each retracted clamp is preferably extended around an associated portion of needle 1 and is closed before the previously extended clamp opens, so that the needle is held continuously by at least one of clamps 3 throughout the handle actuation cycle.

If it is desired to release needle 1 from suturing device 112 at any time during, before, or after a handle actuation cycle, release can be effected by pressing on release input button 16. Pressing on button 16 causes spring-loaded fixing arm 17 to lift away from driven wheels 10 and 12, thereby resetting the clamps in their proximal opened configuration.

Figure 5:
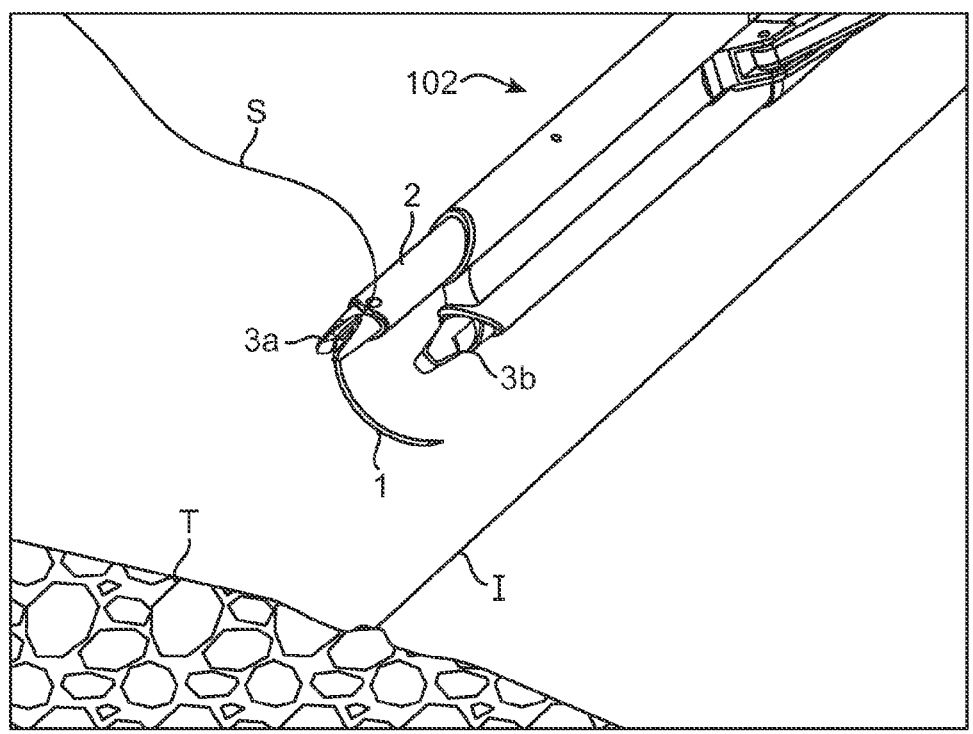
FIGS. 5-9 are perspective views showing use of the device of FIG. 1 for suturing tissues.

Referring now to FIGS. 5-9, the use of suturing device 102 for suturing an incision I in tissue T can be understood. Initially, handles 6, 8 (see FIG. 1) are in a closed-handed configuration and the handles are grasped by a hand of a surgeon. Needle 1 is supported by a first clamp 3a, with the first clamp grasping a proximal portion of the needle adjacent a suture S. The second clamp 3b is retracted proximally away from needle 1, so that a distal portion of the needle is free and exposed, as illustrated in FIG. 5.

Figure 6:
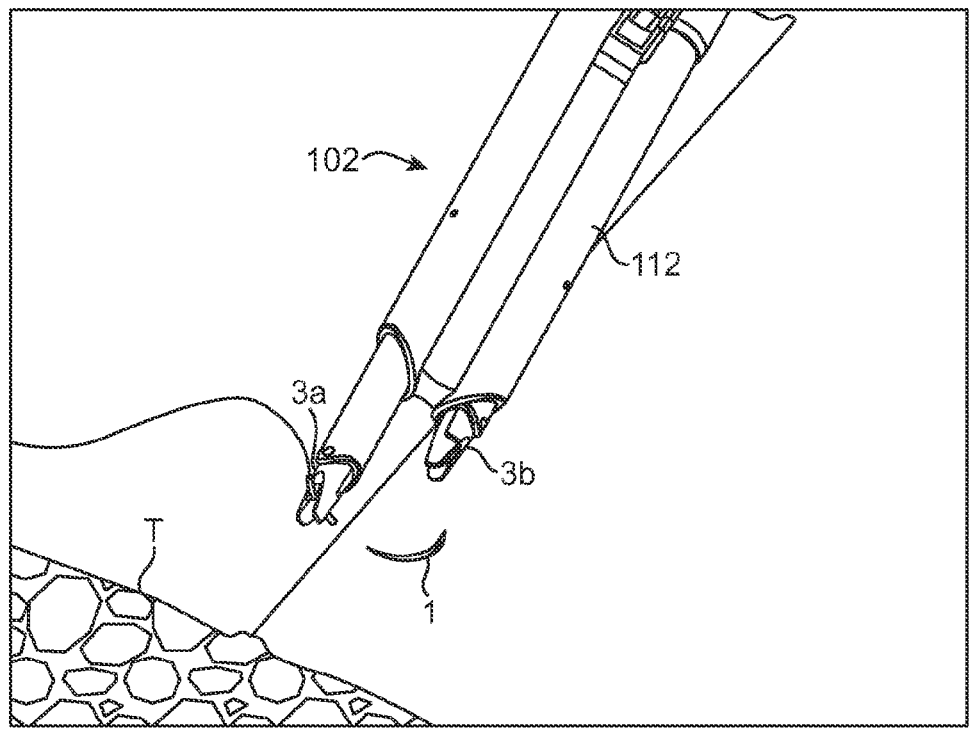
Figure 7:
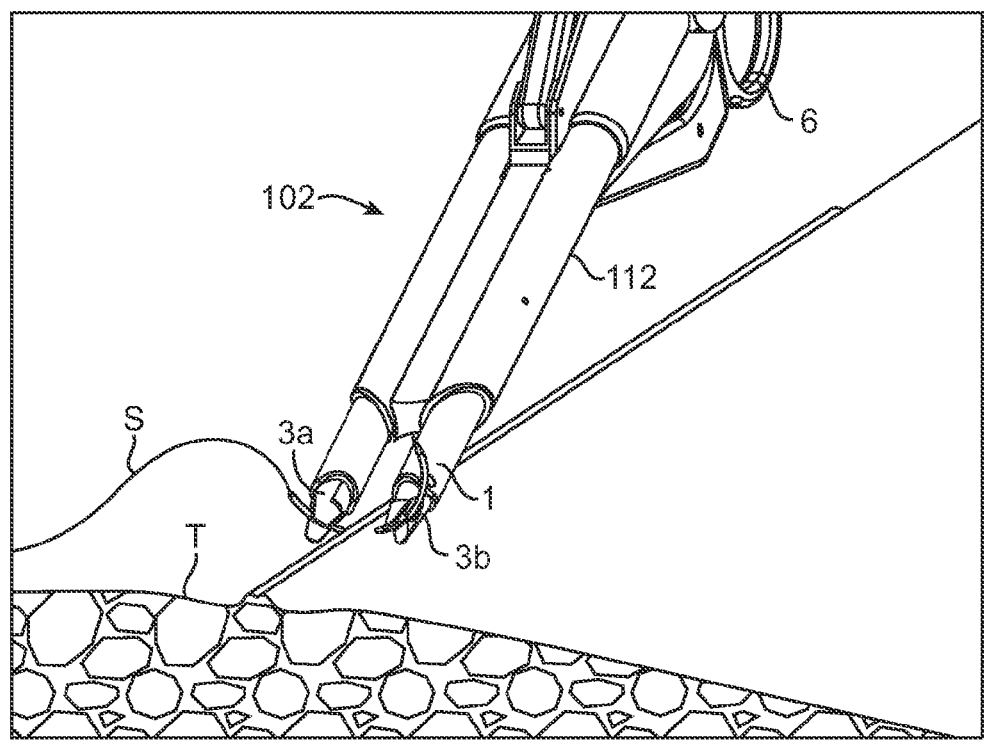

As can be understood with reference to FIG. 6, the surgeon manually moves suturing device 102 by manipulating handles 6, 8 so as to insert a distal portion of suturing needle 1 through tissue T. Advantageously, body 112 and linkage 116 (see FIG. 2) of suturing device 102 inhibits relative movement of needle 1 relative to the body and handles 6, 8 of the suturing device while the handles are closed. This allows the surgeon to precisely control movement of the needle 1 as it is inserted through the tissue, in a manner analogous to manual manipulation of the needle using a standard needle grasper or forceps. As can be understood with reference to FIGS. 6 and 7, once the distal portion of needle 1 extends sufficiently through the tissue, handles 6, 8 can be cycled through at least a portion of their actuation cycle. Through the linkage 116, second clamp 3b is extended distally from body 112 of suturing device 102, grasping the distal portion of needle 1. The first clamp 3a then releases needle 1 and is withdrawn proximally from around the needle, as illustrated in FIG. 8.

Figure 8:
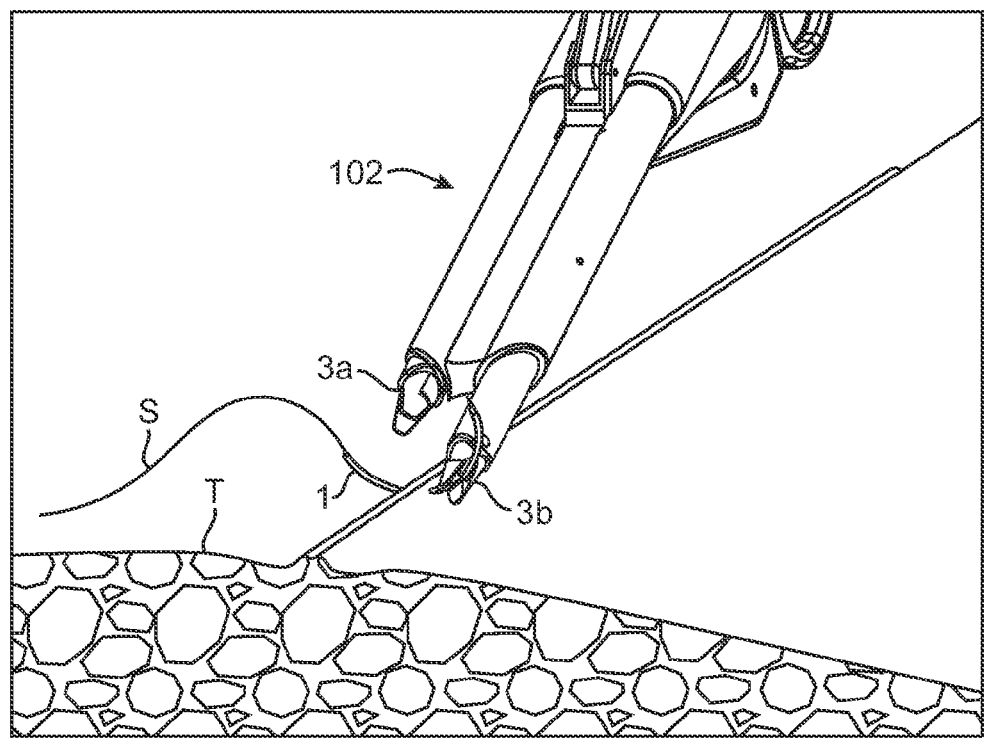
Figure 9:
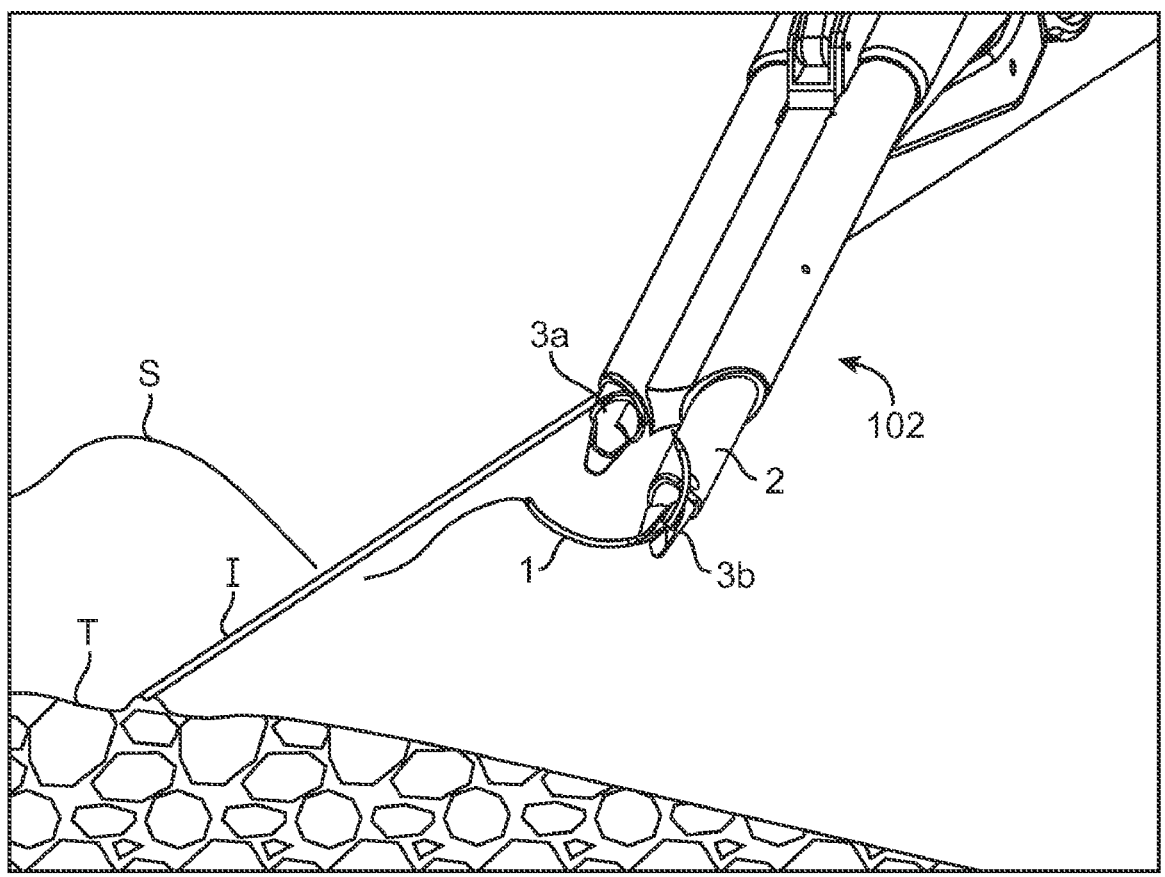

As can be understood with reference to FIGS. 8 and 9, once needle 1 is held by second clamp 3b, the surgeon can again manipulate the needle by moving handles 6, 8. In some embodiments, the surgeon can grasp the handles in an open-handed configuration while pulling the needle free from the tissue, while in other embodiments the needle will be pulled after the handle has returned to the closed-handed configuration. Regardless, the surgeon uses the handles, body, and clamp 3b to pull the proximal portion of needle 1 through tissue T, thereby leaving suture S inserted across incision I.

Prior to initiating a second stitch, the surgeon can cycle handles 6, 8 by closing the handles with his/her hand, or by opening and closing the handles through a full actuation cycle. This results in grasping of needle 1 by first clamp 3a and release of the needle by second clamp 3b, exposing the distal portion of the needle and displacing the second clamp from the needle so that the needle is ready to again insert through tissue T, as can be understood with reference to FIG. 5. The process can then be repeated without ever having to completely release needle 1, and by simply actuation of handles 6, 8 after insertion of the distal portion of the needle through the tissue and again after each pulling of the needle free. The process is repeated to form as many stitches as is desired. Analogous insertion of the distal portion of the needle through loops of suture, actuation of the handle, and pulling the needle free can be used to quickly and easily form knots.

As can be understood from the illustrations in FIGS. 5-9, and as may be indicated by the detailed description above of the articulation of the drive linkage, shafts 2 extending distally from body 112 to clamps 3a, 3b may move slightly during the handle actuation cycle, for example, with the shaft supporting the clamp initially holding needle 1 retracting slightly into body 112 as the other shaft extends. Nonetheless, each clamp holds the needle at a fixed location while the surgeon holds the handles 6, 8 in the closed configuration and inserts or withdraws the needle into or from the tissue.

Figure 10:
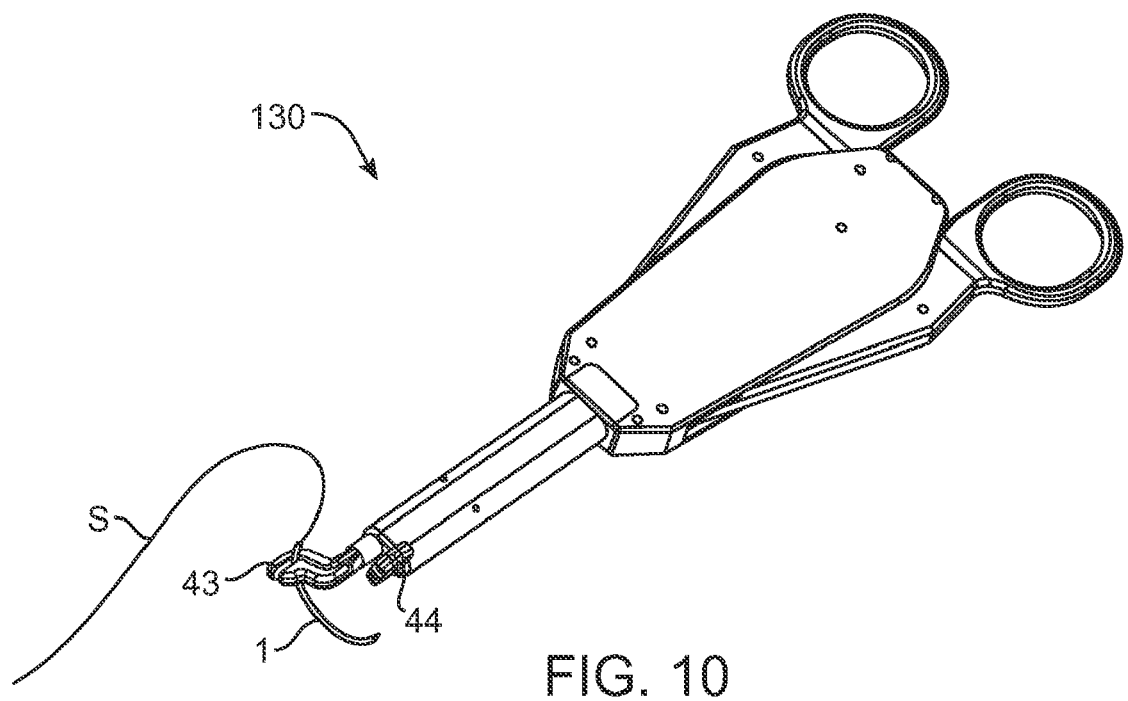
FIG. 10 is a perspective view of an alternative suturing device having first and second clamps which both reciprocate and rotate away from a suturing needle after releasing of the needle from the clamp.
Figure 11:
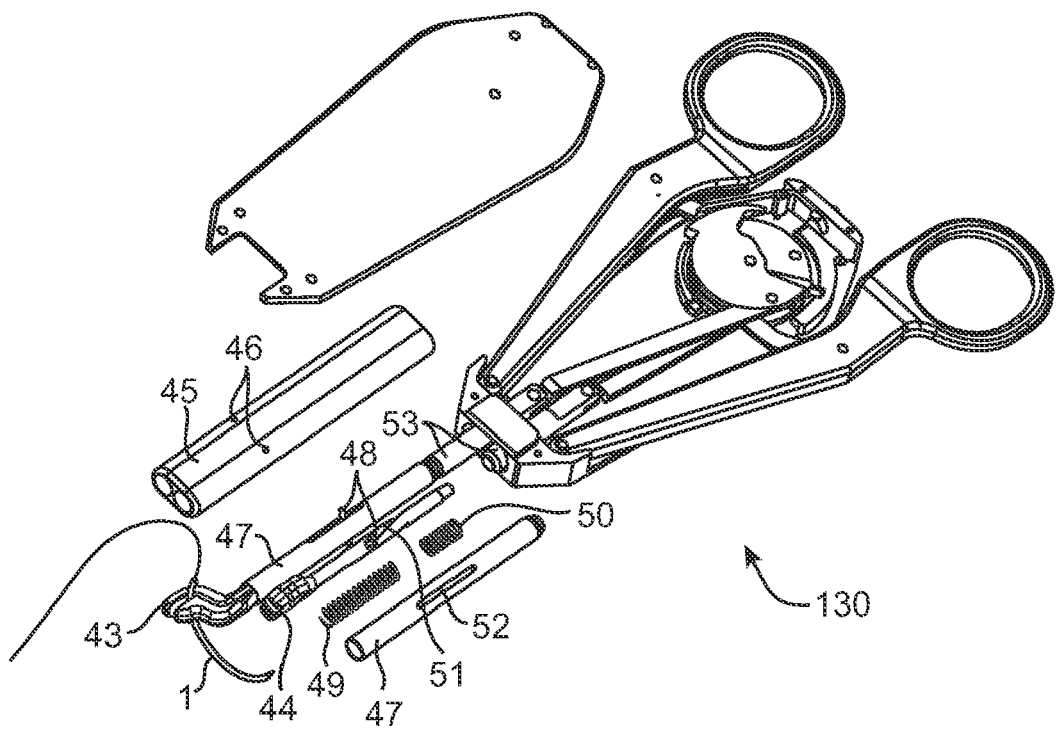
FIG. 11 is an exploded view of the suturing device of FIG. 10 showing some of the components of its drive linkage.

Referring now to FIGS. 10-22, a wide variety of alternative linkage mechanisms, clamp structures, housing, handles, and the like may be employed. Referring first to FIG. 10, an alternative suturing device 130 may include clamps 43, 44 which both retract proximally and rotate away from needle when not used to hold the needle. Referring now to FIGS. 10-17, and avoiding describing structures which are substantially similar to those described above, clamps 43 and 44 have bent-shaped inserts 54 made of a hard alloy (see FIG. 15). Proximal ends of clamps 43 and 44 may have conical surfaces 55 which are located, sized, and configured so as to interact with a distal port of shaft 47, and more specifically, so that proximally withdrawing the working jaws of clamps 43, 44 into sleeve 47 closes the working jaws of these clamps.

Shaft 47 has a lengthwise slot 52 for receiving a guiding pin, while a proximal extension of the working jaws of clamps 43, 44 has a spiral lengthwise slot 51 receiving guiding pin 48. Shafts 47 are connected with pushers 53, and ride in distal body extension 45, with the distal body extension again having openings for receiving the guiding pins.

In alternative suturing device 120, as the guiding pins 45 ride within spiral slot 51 due to axial motion of clamps 43, 44, the clamp rotates away from a needle 1 about the axis of shaft 47 when the clamp retracts proximally.

Figure 12:
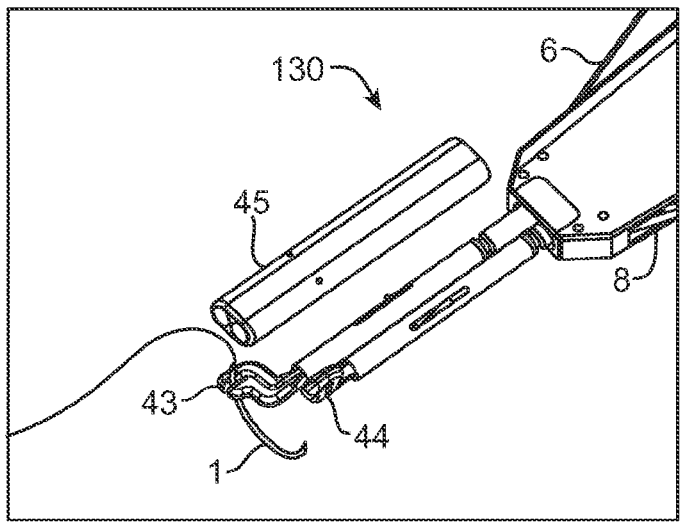
FIGS. 12-14 are partially exploded perspective views showing a portion of an actuation cycle of the suturing device of FIG. 10, and showing how the clamps both reciprocate and rotate away from the suturing needle.
Figure 13:
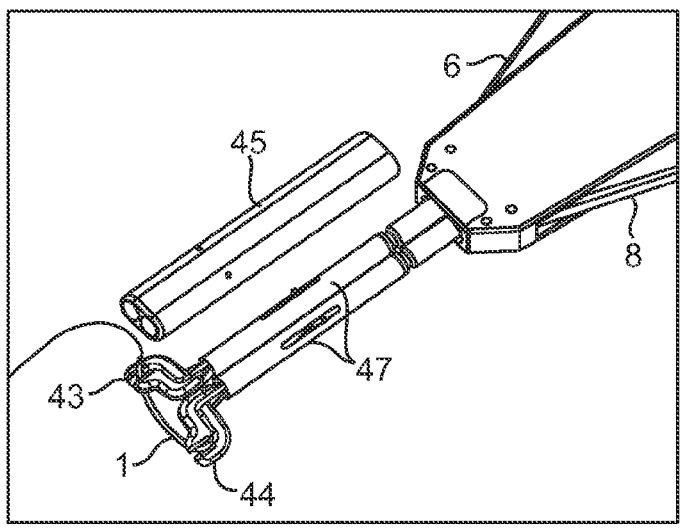
Figure 14:
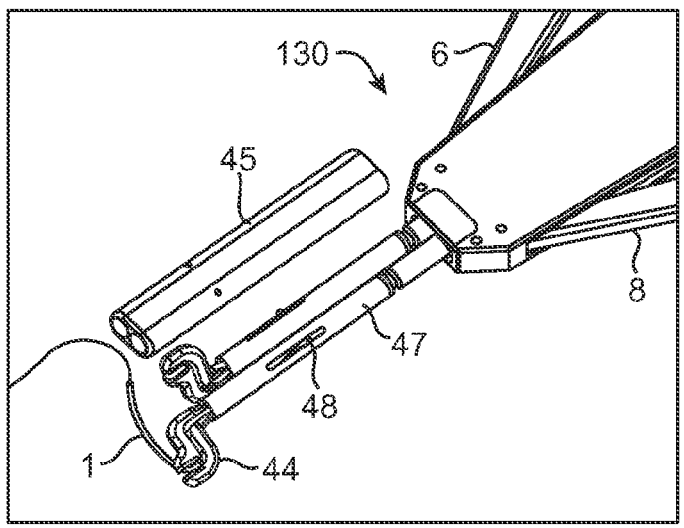
Figure 15:
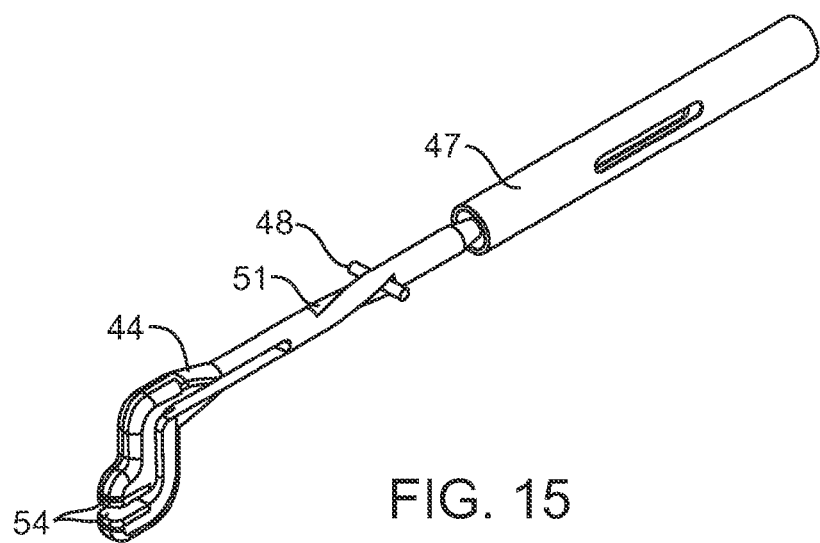
FIGS. 15-17 are perspective views of components of the suturing device of FIG. 10, showing how rotation of the reciprocatable shaft is effected.
Figure 16:
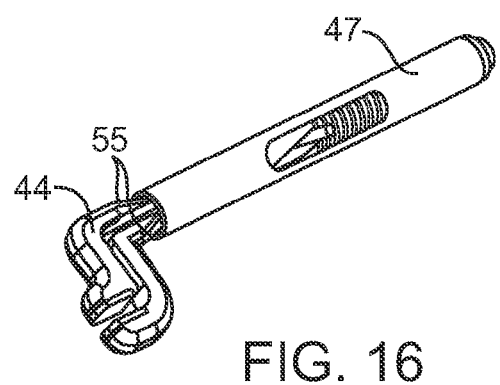
Figure 17:
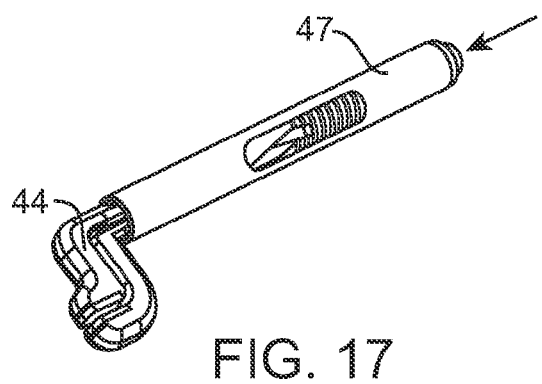

The rotation of clamps 43, 44 with axial movement of shafts 47 as effected by actuation of handles 6, 8 can be understood with reference to FIGS. 12-13. As can be seen in FIG. 12, a first rotatable clamp 43 holds a proximal portion of needle 1 while handles 6, 8 are in a closed-handed configuration, while second rotatable clamp 44 is both withdrawn proximally and rotated clear of the needle. As the handles begin to open, as illustrated in FIG. 13, distal movement of shaft 47 of second rotatable clamp 44 imparts a twisting motion to the clamp due to the interaction between the guiding pin 48 and the helical slot 51 (see FIG. 11). The second rotatable clamp 44 can rotate into position and extend around needle 1, with the second clamp 44 grasping needle 1 and first clamp 43 withdrawn proximally and rotated free from the needle when the handles are in their fully opened configuration. Once again, a full actuation cycle from a closed configuration to an open configuration and back to a closed configuration may result in the needle alternating from being grasped by the first clamp along a proximal portion of the needle, then being grasped by the second clamp along a more distal portion of the needle (with the handles in the open configuration), and with the needle again being grasped solely by the first clamp when the handles are returned to the closed configuration. The structure and rotation of rotatable clamps 43, 44, along with the associated interaction between shaft 47 and guiding pin 48 are also illustrated in FIGS. 15-17.

Referring now to FIGS. 18-21, a still further alternative suturing device 140 has first and second clamps 142, 144 formed by working jaws 56, 57 connected at an axle 58. The shafts supporting clamps 142, 144 here comprise flattened structures 60 located within channels of body extension 61. Shafts 60 interact with rods 67 of pusher 63. This linkage couples handles 62 to clamps 142, 144 using a moveable rod 65 and an immovable fixing arm 66, along with a flat spring 64. Rods 67 of pushers 63 have inclines 68 which function to open and close the clamps, as can be understood with reference to FIGS. 20 and 21.

Note that in embodiment 140, needle 1 generally extends along a plane of actuation of handle 62. In contrast, in suturing device 102, illustrated in FIG. 1, needle 1 generally extends across the handle actuation plane. Ergonomically, there may be advantages in orienting the needle so that it traverses the handle actuation plane as shown in FIG. 1. Such a configuration may conveniently be used by either a right hand or a left hand of the surgeon, although embodiments configured for use by only one or the other may also be provided.

Figure 18:
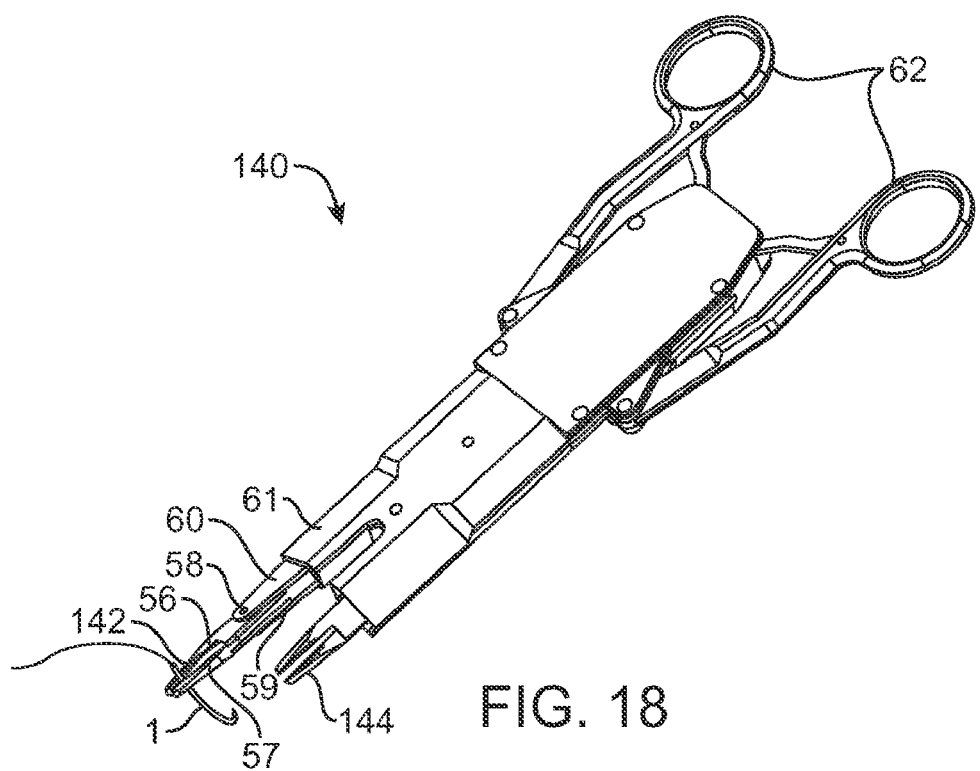
FIG. 18 is a perspective view of another an alternative suturing device which holds a suture needle so that an axis of the needle extends along an actuation plane of a handle of the device.
Figure 19:
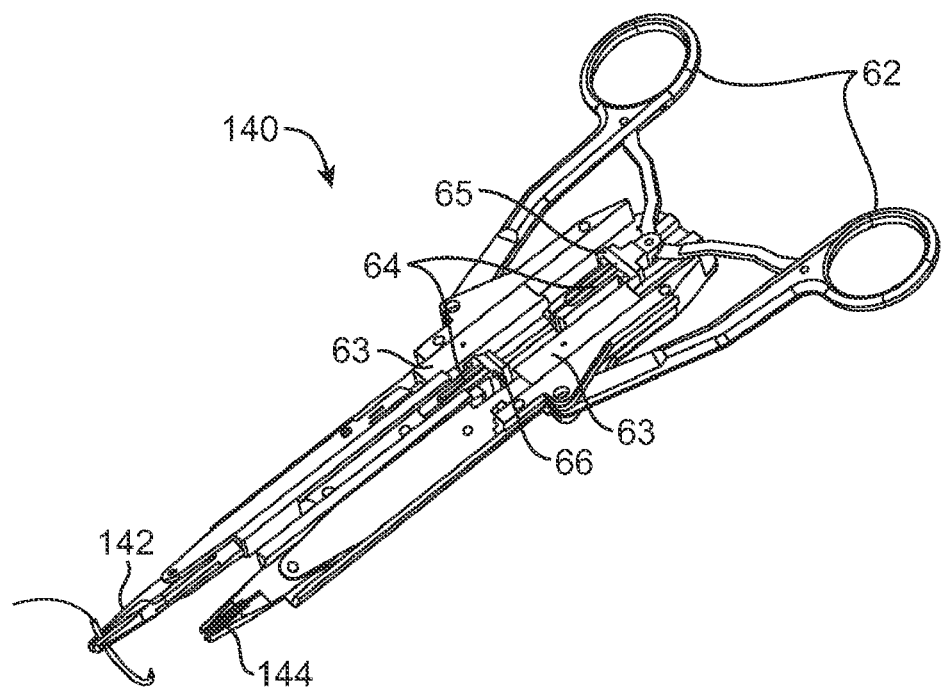
FIG. 19 is a perspective view of a suturing system including the suturing device and needle of FIG. 18, with a cover removed so as to show components of a linkage coupling the actuatable handles of the device to clamps for holding the needle.
Figure 20:
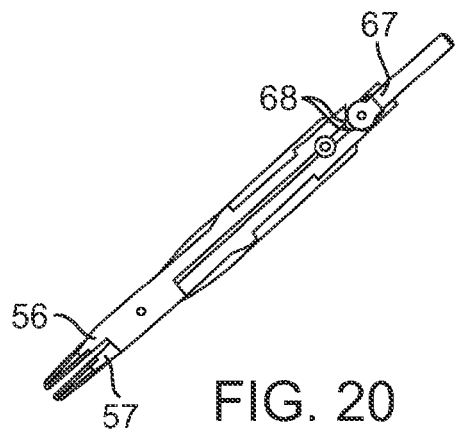
FIGS. 20 and 21 are detailed views illustrating reciprocatable shafts and drive linkages configured to effect movement and actuation of the clamps in the suturing device of FIG. 18.
Figure 21:
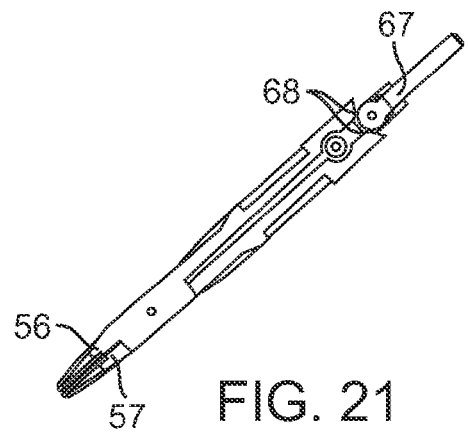
Figure 22:
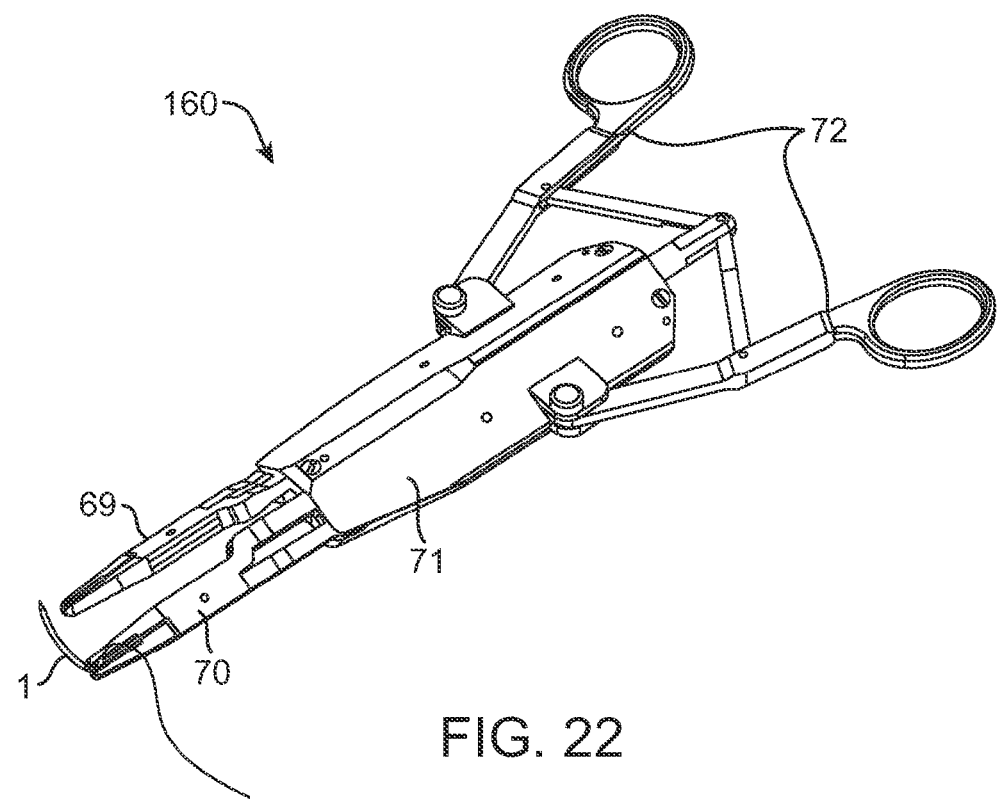
FIG. 22 is a perspective view of yet another alternative suturing device and system having a drive system including a rack and cams.
Figure 23:
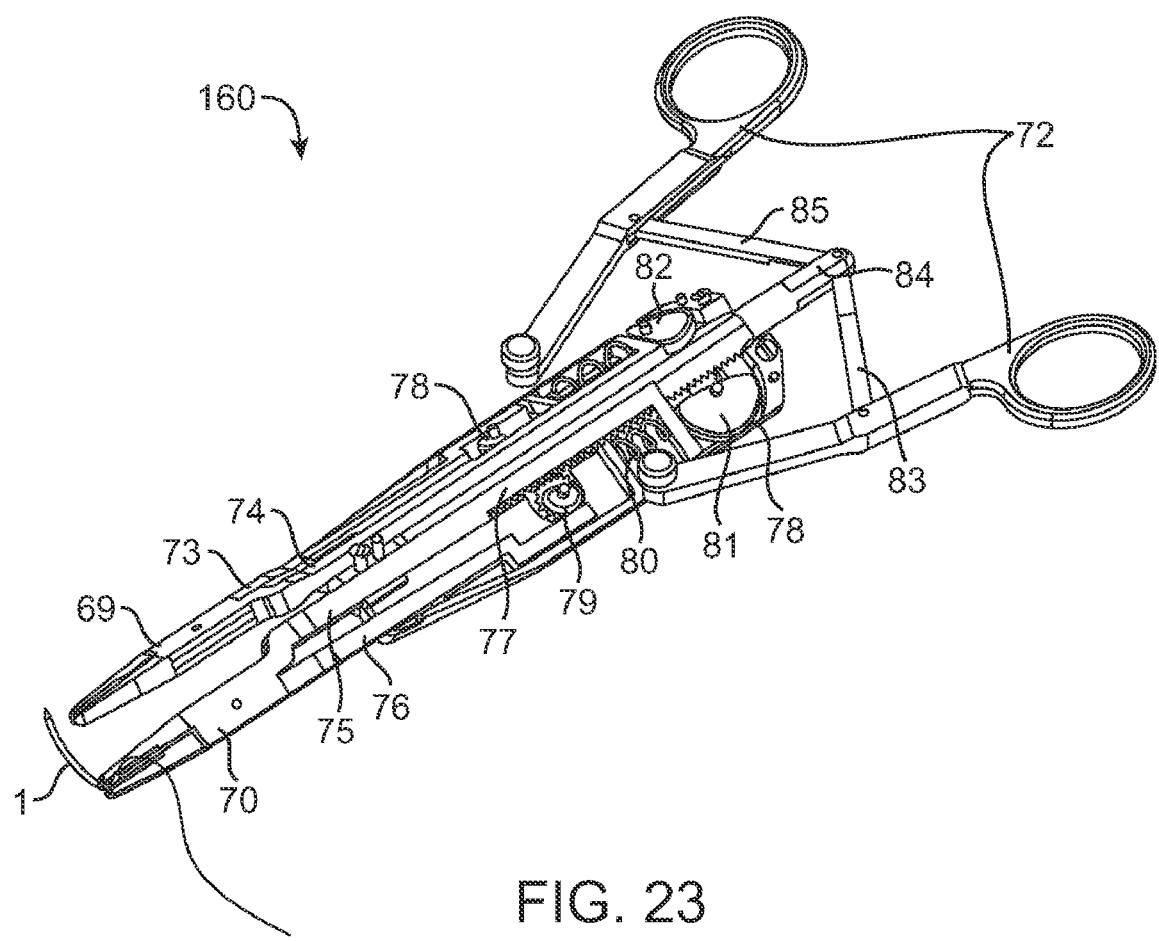
FIG. 23 is a perspective view of the suturing device of FIG. 22 with a cover removed so as to show components of the drive system of the device.

Referring now to FIGS. 22 and 23, yet another alternative suturing device 160 has an external appearance somewhat similar to suturing device 140 of FIGS. 18 and 19, but makes use of a significantly different linkage mechanism for coupling handle 72 to clamps 69, 70. The clamps again extend from associated channels in body 71, but the linkage here makes use of a rack 77 actuated by a rod 84.

First clamp 69 has elongate levers 73 and 74, while second clamp 70 has levers 75 and 76. Tie rods 83 and 85 axially actuate rack 77 via rod 84, resulting in rotation of cams 78, 79, and large cams 81, 82. The large cams axially extend associated levers 74 and 75 so as to axially extend their associated clamps, while a spring 80 proximally withdraws the clamps when allowed by their cams. The small cams open and close the clamps via levers 73 and 76, with the levers generally acting as followers along the cam surfaces.

Figure 24A:
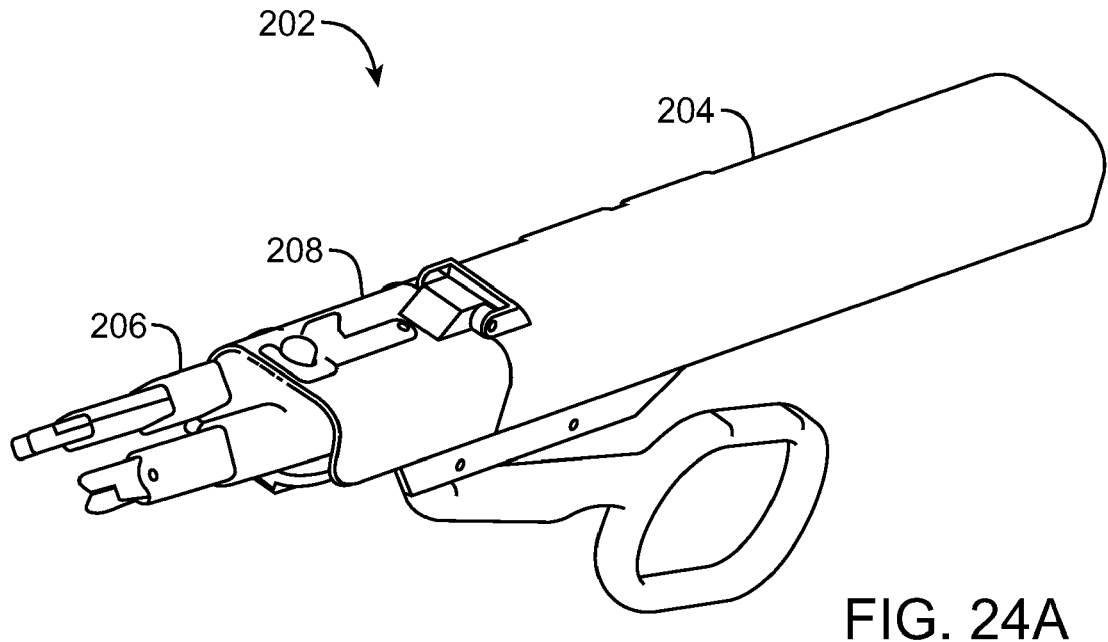
FIGS. 24A and 24B illustrate an exemplary suturing device in which the clamps are releasably coupled to the body of the device, allowing the clamps to be disposable to avoid cross contamination between differing patients without having to sterilize the clamp structures.
Figure 24B:
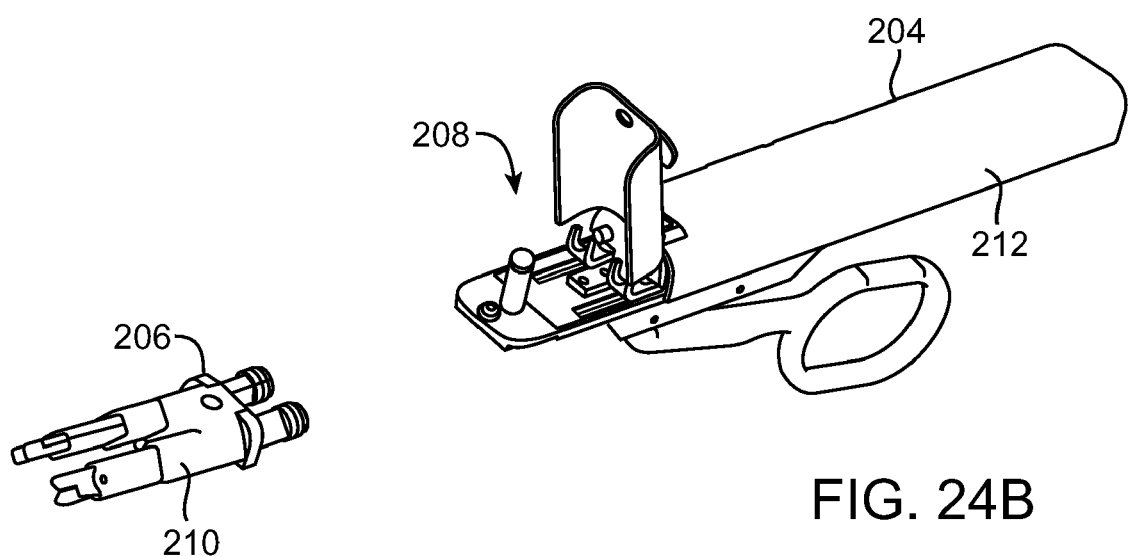

Referring now to FIGS. 24A and 24B, an alternative suturing device system 202 may include many functional components which are similar to those described above, but can generally be separated into a reusable drive unit 204 and a disposable clamp unit 206. A releasable coupler 208 releasably couples clamp unit 206 to the drive unit 204. The exemplary coupler includes an interface that provides rigid coupling between extensions 210 of the clamp unit 206 and proximal housing 212 of drive unit 204, and also provides moving engagement surfaces between the shafts of the clamp unit and axially moving elements of the drive linkage. While the exemplary releasable coupler 208 includes axial positioning surfaces (in the form of a pin of drive unit 204 and corresponding aperture of clamp unit 206) and a releasable latch to avoid inadvertent decoupling, a wide variety of alternative releasable couplers might also be employed. The exemplary clamp unit includes two clamps. In some embodiments, each clamp may be individually attached to a drive unit 204. Regardless, allowing the clamps to be detached from the drive unit can avoid any need for making the clamps sterilizable, decreasing overall costs of the suturing system and helping to ensure that cross-contamination between patients is inhibited. A plurality of clamp units 206 will often be used with each drive unit 204, with each clamp being used for a single patient and then being disposed of.

Figure 25A:
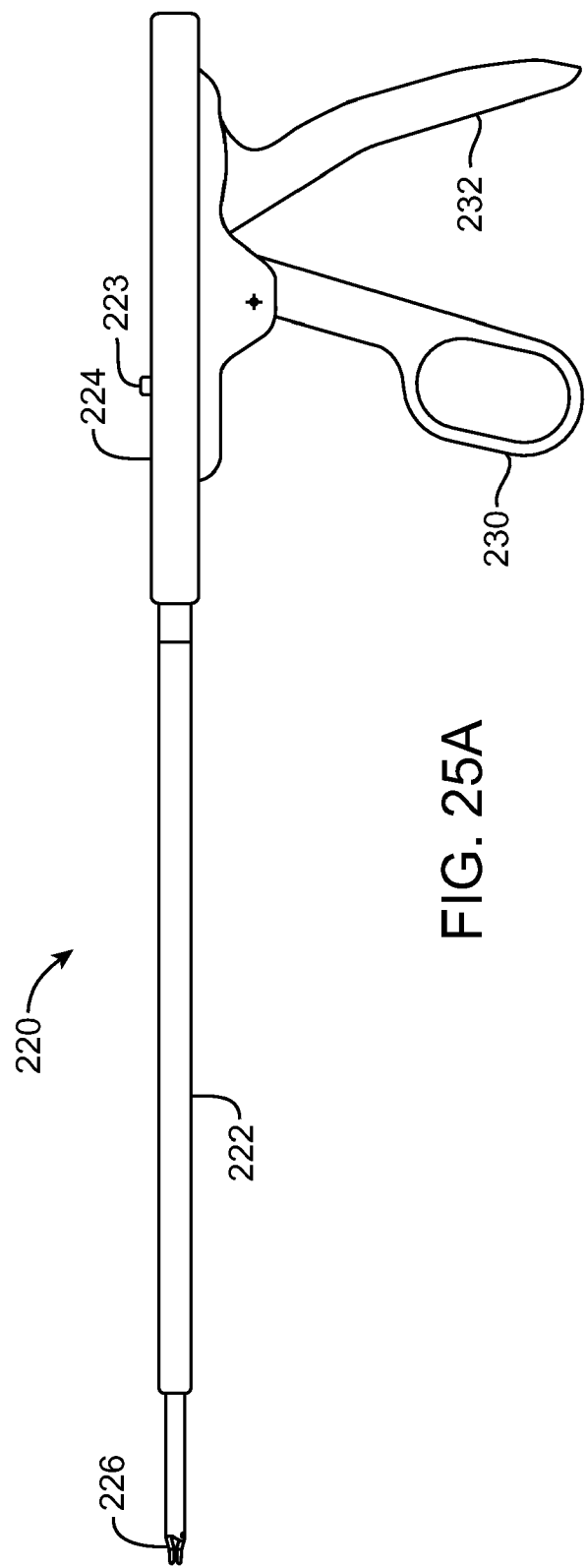
FIGS. 25A and 25B are a side view and top cross-sectional view, respectively, of another embodiment of a suturing device having a drive linkage with an alternatable drive element for moving first one clamp and then the other, and also having an alternatable latch for inhibiting movement of the clamp that is not being driven.
Figure 25B:
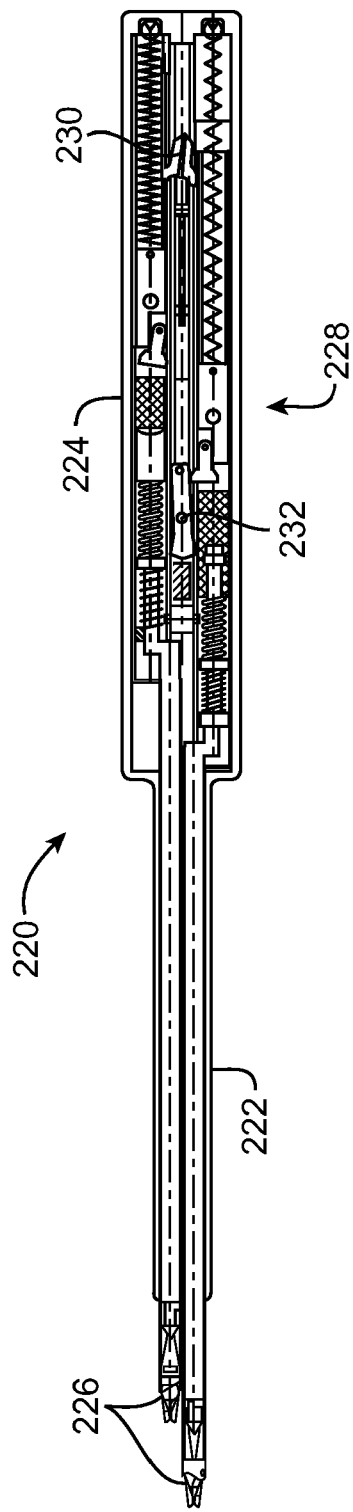

A still further exemplary suturing device embodiment 220 can be seen in side and cross-sectional top views in FIGS. 25A and 25B. An elongate extension 222 coupling proximal housing 224 to clamps 226 may facilitate use of suturing device 220 in endoscopic surgery or the like. In this embodiment, actuation of drive linkage 228 is generally effected by movement of a single articulatable handle 230 relative to a grasping base 232 that is affixed to proximal housing 224. By allowing the surgeon to grasp a structure that remains rigidly affixed relative to the suturing device body with one portion of the hand, and articulate handle 230 with the fingers of that hand, the overall position of suturing device 220 (and clamps 226, along with any needle supported therein) can be accurately maintained. As with the other embodiments described herein, a release 233 will often be provided that, when actuated, releases a needle from both clamps and sets the two clamps in a needle-receiving configuration.

The components and use of drive linkage 228 of suturing device 220 can be understood with reference to FIG. 26 and FIGS. 26A-26M. As generally described above, drive linkage 228 includes an alternatable drive element 230 for alternating the driving of first one and then the other of the two clamps. Additionally, drive mechanism 228 includes an alternating latch or anchor 232 for inhibiting axial movement of the clamp that is not currently being driven. Drive linkage 228 further makes use of a channel casing 234 in which a movable tubular shaft 236 slides along an axis 238. First and second pushers 240, 242 and a cone with a rod 244 are disposed along axis 238, while a striker 246 and a stop pin with a spring 248 are disposed off of axis 238.

Figure 26:
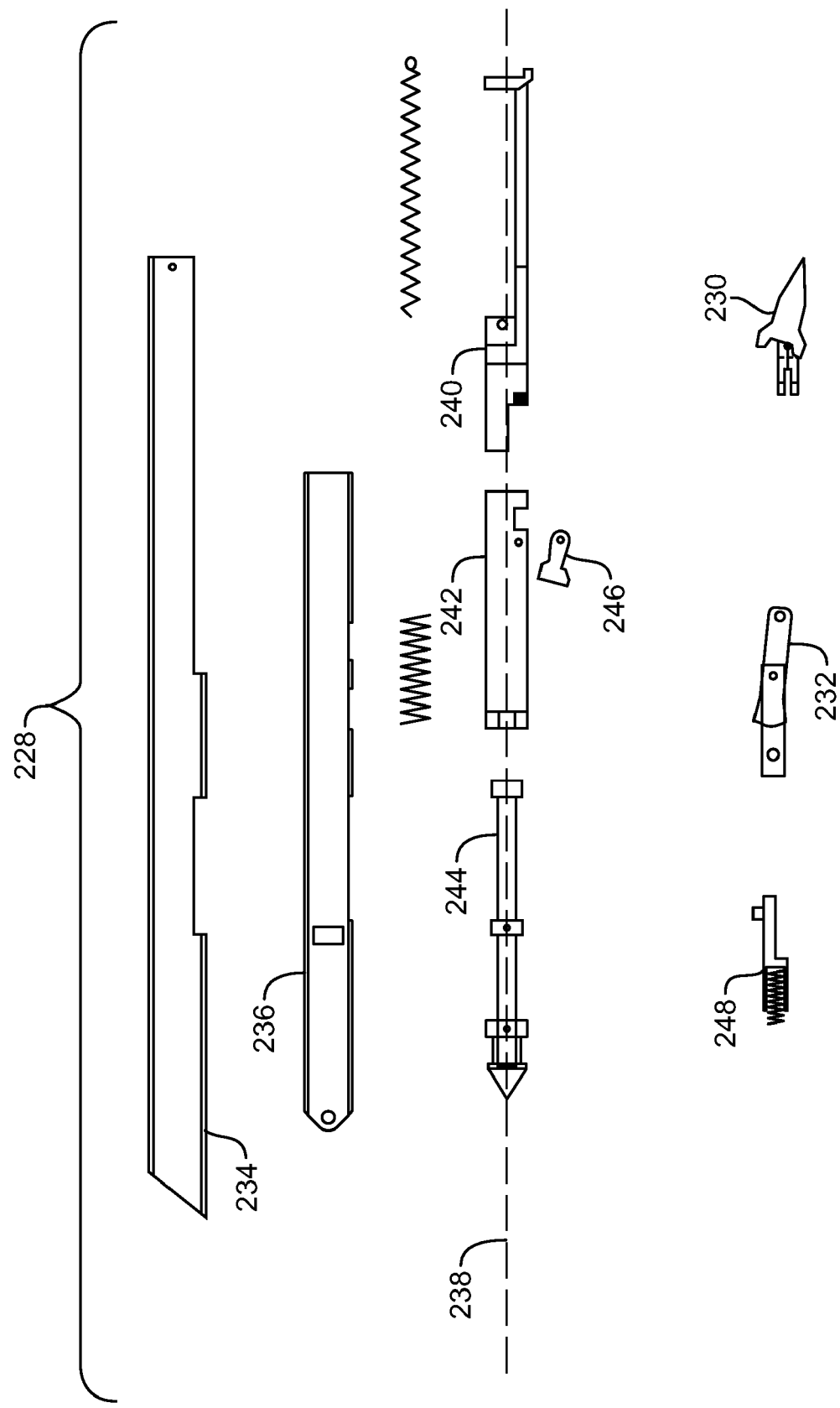
FIG. 26 is an exploded view schematically showing some of the components of the drive linkage of the suturing device of FIGS. 25A and 25B.
Figure 26A:
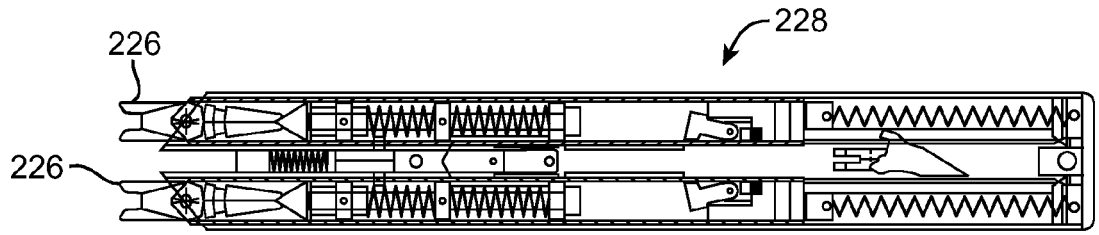
FIGS. 26A-26M are cross-sectional views schematically illustrating actuation of the linkage of the suturing device of FIGS. 25A and 25B.
Figure 26B:
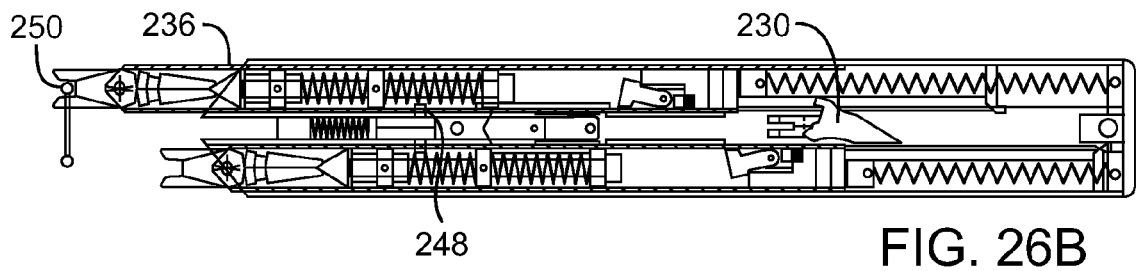

Reviewing the sequence of actuation of these components schematically, FIG. 26A shows the components of drive linkage 228 at a beginning configuration (such as after actuation of the release), with both clamps 226 in a configuration that is open and ready to receive a needle. In FIG. 26B, alternatable drive element 230 drives a first shaft 236 distally along its axis till the shaft engages pin 248. Needle 250 is disposed within the clamp, with the alternatable drive element 230 continuing to move axially with movement of the handle.

Figure 26C:
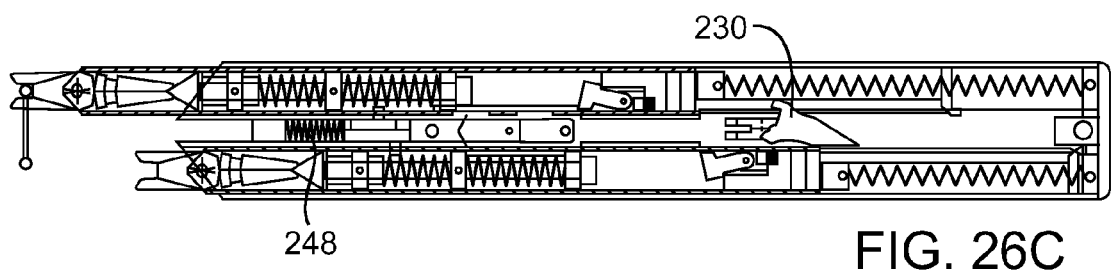
Figure 26D:
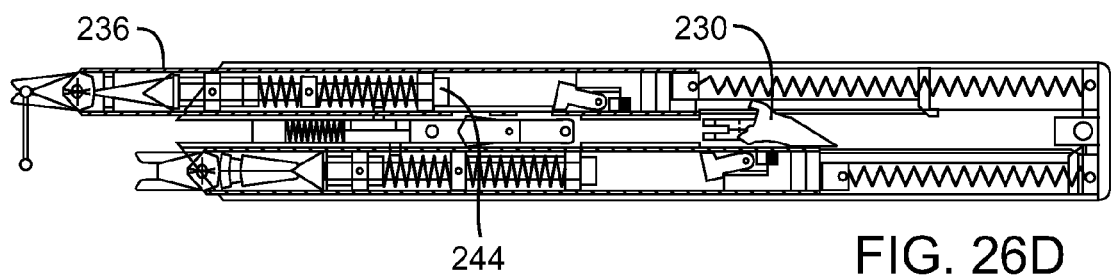
Figure 26E:
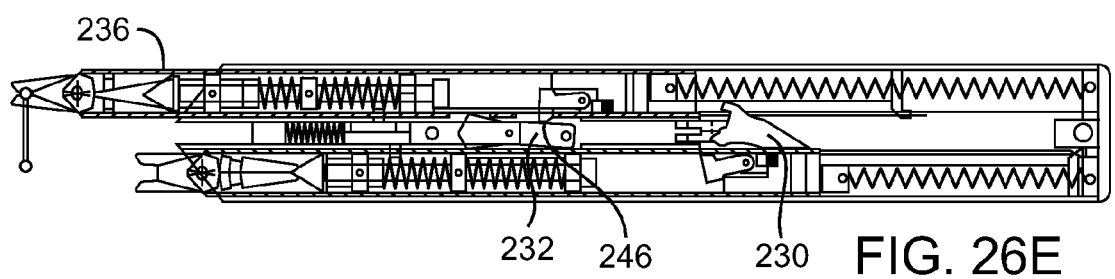
Figure 26F:
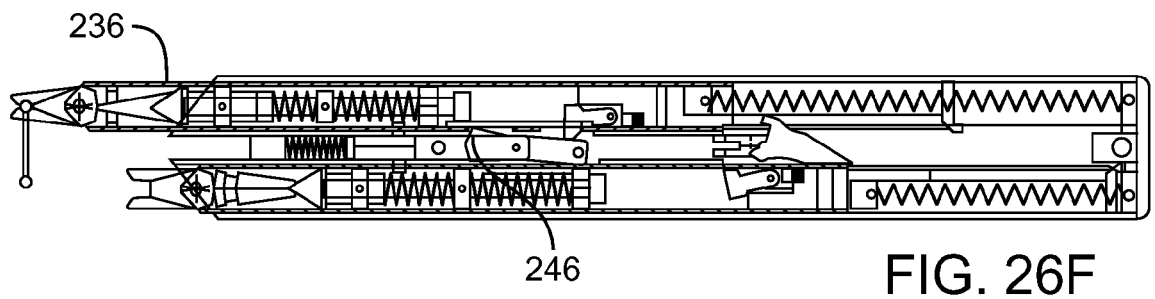
Figure 26G:
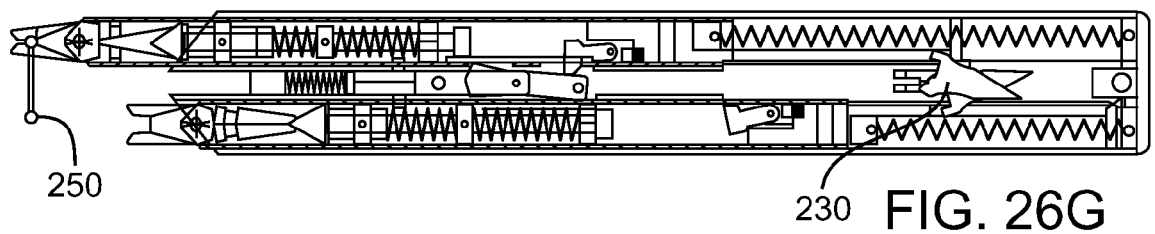

In FIG. 26C, continuing movement of drive element 230 has produced axial movement of pin 248 so as to compress its spring, so that the pin stops moving axially. As a result, continuing movement of drive element 230 does not produce additional movement of shaft 236, but instead causes the cone with its rod 244 to move within the shaft 236 till it reaches its distal position, as shown in FIG. 26D.

Additional movement by drive element 230 results in axial movement of pushers 240, 242, causing the striker 246 to move into alignment with a window in the shaft 236, and thus allowing the striker to engage and reposition latch 232. As the reconfigured latch 232 inhibits proximal movement of shaft 236, the handle may be returned (often to its extended position, as can be understood with reference to FIG. 26F) without movement of shaft 236.

Figure 26H:
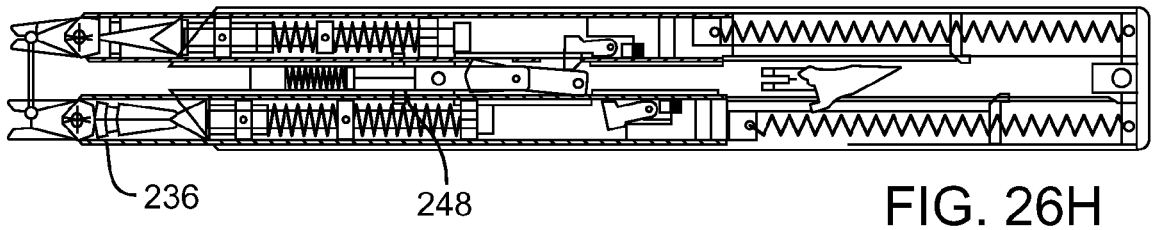
Figure 26I:
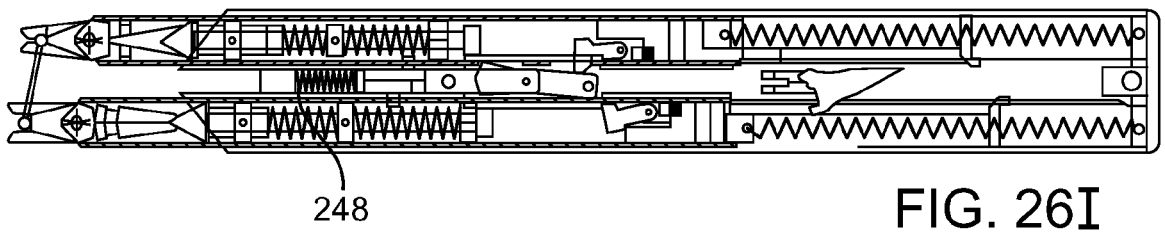
Figure 26J:
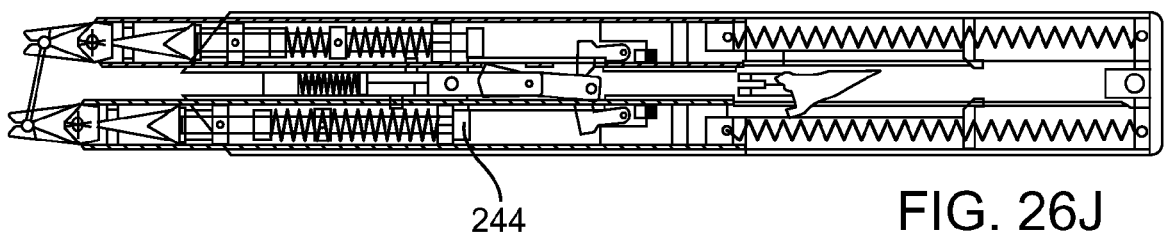

Once the handle returns to its starting or extended position, needle 250 may be inserted into and through the tissue. Returning of the handle also reconfigures alternatable drive element 230 to engage the other, previously non-driven clamp actuation components, with the other shaft 236 again moving distally along its axis due to movement of the handle to engage and compress pin 248 (as seen in FIGS. 26H and 26I), inducing axial movement of the cone and rod 244 and allowing the associated striker to again reconfigure the alternatable latch 232 (see FIGS. 26J and 26K). Reconfiguring the latch allows the extended, non-driven clamp 226 to retract proximally to the configuration shown in FIG. 26L under the influence of its proximal return spring, this retraction optionally occurring quite quickly. The handle may now again be released, with the reconfigurable drive element 230 again being reset to alternate the driven and latched clamps, as shown in FIG. 26M.

Figure 26K:
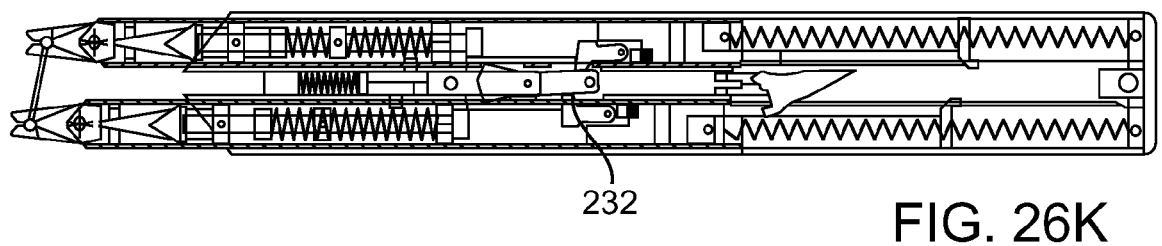
Figure 26L:
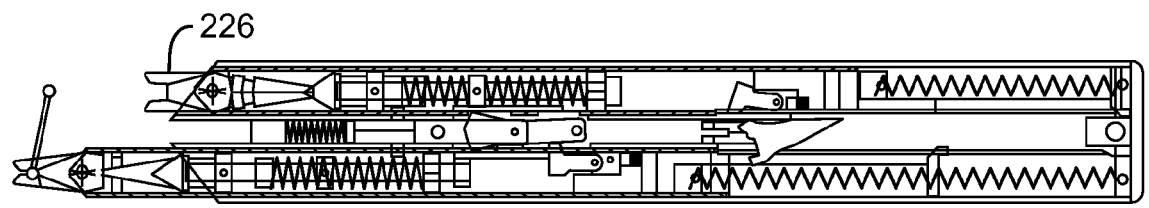
Figure 26M:
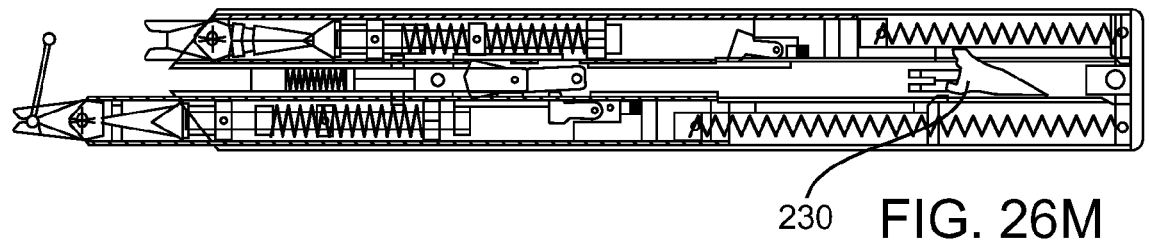

Structures and methods which inhibit gradual displacement of needle 250 relative to suturing device 220 during repeated cycling of drive linkage 228 can be understood with reference to FIGS. 26I and 26K. As each clamp 226 is extended to grasp needle 250, the clamp advances distally slightly beyond the eventual location at which the clamp will hold the needle for suturing. This stresses and/or displaces the needle slightly, and the clamp then grasps the needle at the extended location. The extended location will typically be less than 20 diameters of the needle past the other clamp, typically being a few needle diameters distal of the other clamp (smaller needles generally employing smaller stress-inducing distances). The grasping clamp that is to retain needle 250 is retracted slightly to the grasping location and the other clamp is opened, so that needle 250 is positioned for the next cycle, i.e., so that the other clamp will again stress the needle before it is grasped. This slight alternating overshoot during grasping of the needle helps maintain the needle near the proximal end of the grasping jaws during cycling. The needle may also be manually pre-angled by the surgeon, either proximally or distally, to facilitate proximal or distal suturing. For example, the distal tip of the needle may extend or angle distally of the grasping clamps, rather than the needle being disposed perpendicular relative to the axes of the shafts. Cycling of drive linkage 228 will largely reproduce and maintain the grasping angle as the clamps alternatingly grasp the needle, with some gradual trend toward a perpendicular needle induced by the alternating overshoot during large numbers of actuator linkage cycles (for example, with movement of the distal portion of the needle proximally along the jaws by a few needle diameters or less with each cycle). Hard metal inserts with small protrusions or teeth along the grasping jaw surface may also be beneficial to limit inadvertent movement of the needle relative to the jaws.

Figure 27A:
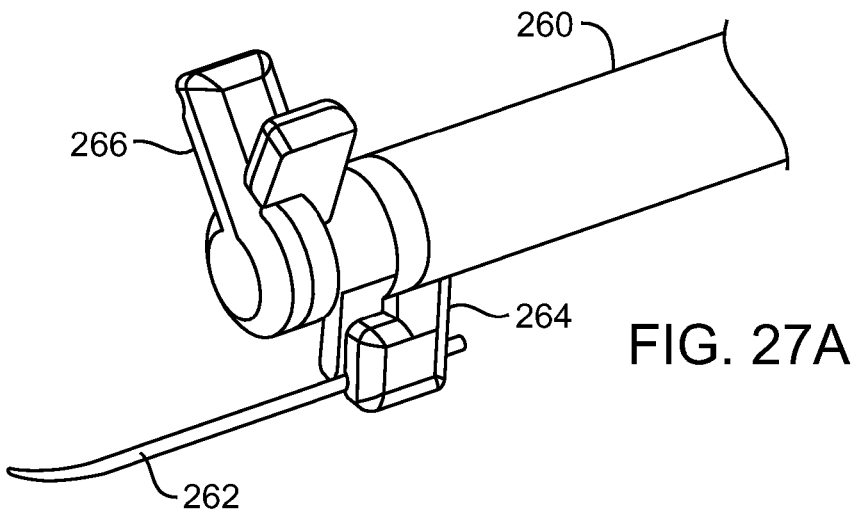
FIGS. 27A-27C are perspective views of a distal portion of an alternative suturing mechanism in which axially offset clamps alternately grasp proximal and distal portions of a ski-jump suturing needle.
Figure 27B:
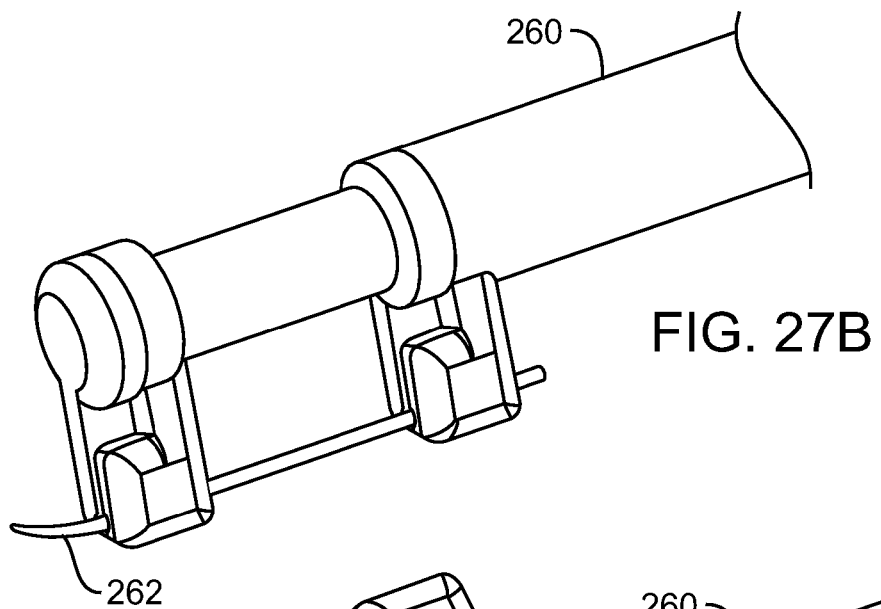
Figure 27C:
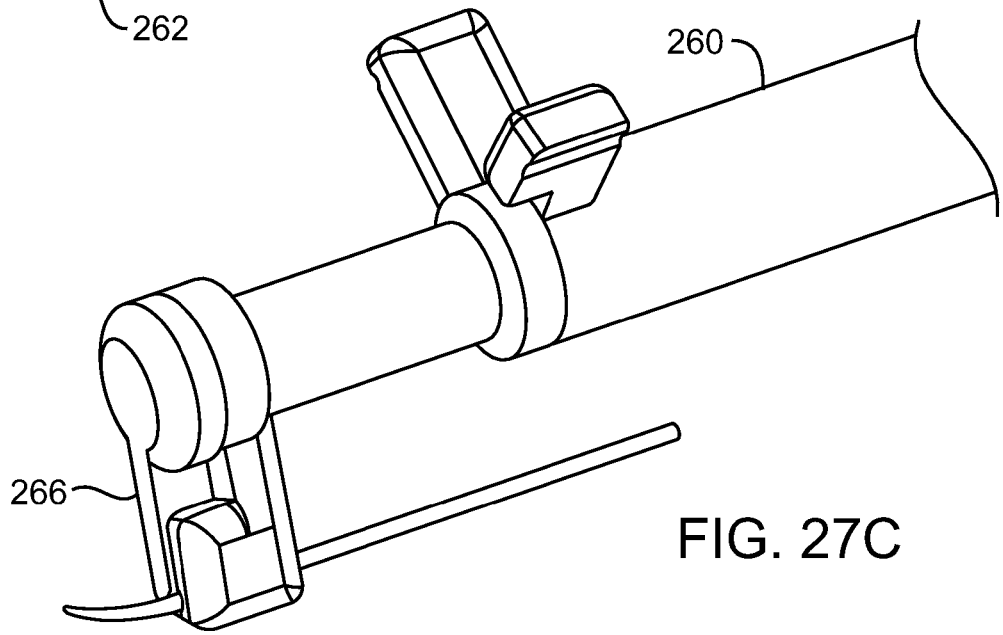

Referring now to FIGS. 27A-27C, a wide variety of alternative suturing device clamping arrangements may also be employed. An axially concentric suturing device 260 is particularly well suited for use with a ski-jump needle 262. Such needles may comprise a proximal straight section and a distal curving section, and may be commercially available from a number of suppliers with suture affixed thereto (not shown). A proximal clamp 264 and distal clamp 266 have clamping jaw members which separate and rotate away from needle 262 to allow the needle to be inserted into tissue (in the configuration of FIG. 27A). The drive system may transfer the needle between the two clamps (FIG. 27B), and allow the needle to be pulled distally free of the tissue (in the configuration of FIG. 27C), with the clamps opening and closing with the cycling of a handle using drive elements that may be similar to, analogous to, or quite different than at least some of the drive components described above.

Figure 28:
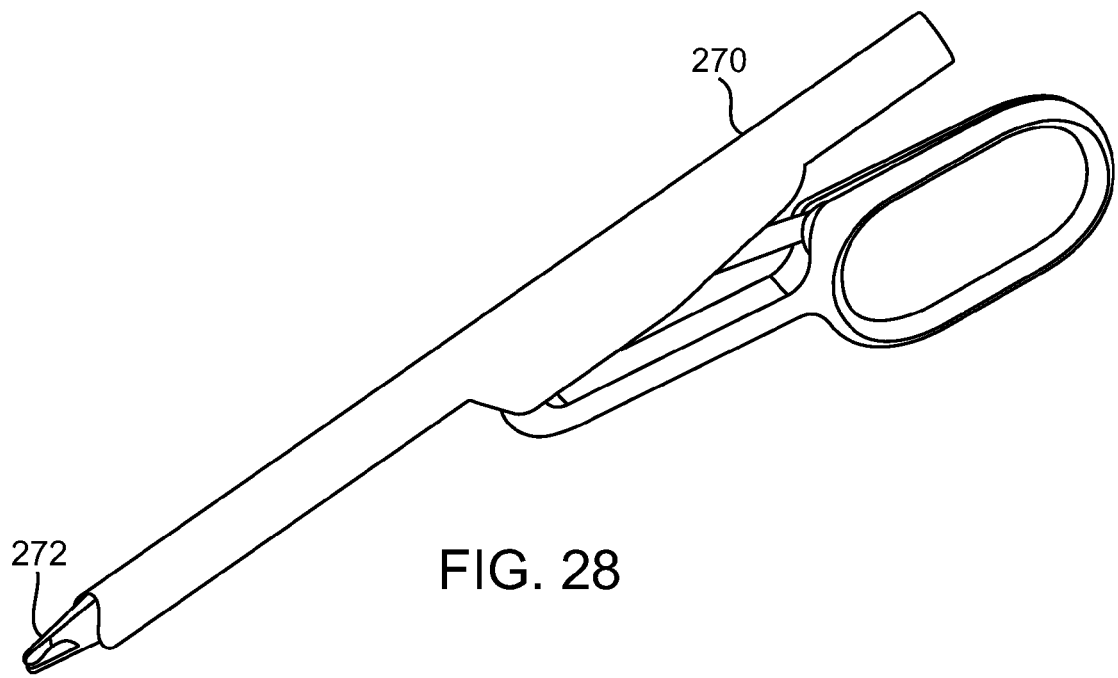
FIG. 28 is a perspective view of an alternative suturing device having a single needle-grasping clamp.

Referring now to FIG. 28, an alternative suturing device 270 may make use of many of the drive components described above, but may include a single clamp 272. Rather than passing a needle back and forth between two clamps, suturing device 270 may be used in a manner analogous to standard needle drivers, and may be particularly well suited for use in the endoscopic or other minimally invasive surgeries.

Figure 29:
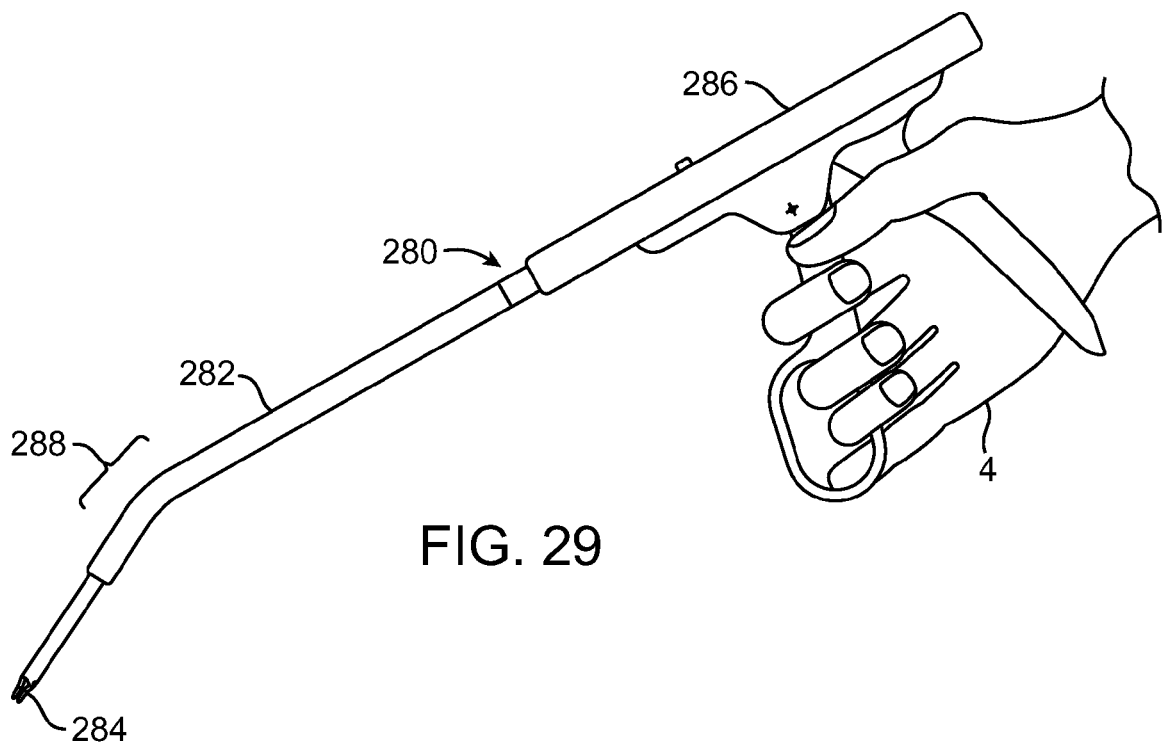
FIG. 29 is a side view schematically illustrating a suturing device similar to that of FIG. 25A in which an extension of the body between the clamps and proximal housing has been manually bent for a particular patient, in which the clamps are actuatable through the bent extension, and which is being grasped by a hand of a surgeon.

FIG. 29 schematically illustrates a suturing device 280 similar to that of FIGS. 25A and 25B, with extension 282 between clamps 284 and proximal body housing 286 here having a bend 288. While such suturing devices may optionally be sold in a pre-bent configuration, bend 288 may alternatively be imposed by a surgeon, with the surgeon manually (or optionally, with the assistance of one or more tools) bending the extension (or another structure supporting the clamps) to a desired configuration for use in a surgical procedure on a particular patient. Extension 282 may be formed of a material (typically comprising a metal or polymer) which can withstand bend 288 while maintaining structural integrity of the suturing device, and the drive components which move within bend 288 (such as the axially movable shaft, rod with a cone, or the like) may be formed of a material (or having a configuration) which can accommodate lateral deflection within the bent tubular extension during the actuation, such as by forming drive components of a suitable polymer, making use of at least a portion of the drive components which are formed as a helical coil, including thin, flexible sheet metal components, or the like. In general, reconfiguring the drive components or support structures to employ bent sheet metal parts may also help reduce manufacturing costs, and the like. Hence, the shaft may (for example) comprise a sheet metal structure with end tabs having openings to receive components therein, and/or the like. The positive control or positioning of clamps 284 which can be available using a grasping base that's originally affixed to the body housing 286 when suturing device 280 is held by a hand H of a surgeon can also be understood with reference to FIG. 29.

Referring now to FIGS. 30A-30D and FIGS. 31A and 31B, methods for tying a knot 302 can be understood. Knot 302 may be particularly advantageous for tying with any of the suturing devices described herein, and may also be employed with other needle drivers and/or suturing devices.

Figure 30A:
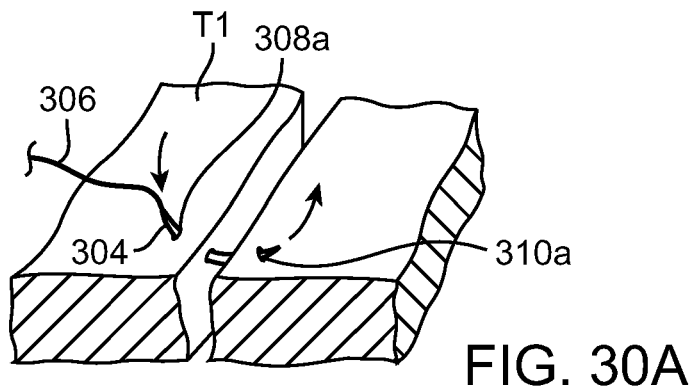
FIGS. 30A-30D are perspective views schematically illustrating steps in tying a knot, where the knot can optionally be tied by manipulating the two-clamp suture devices described herein without the surgeon releasing the suturing device from his or her hand.
Figure 30B:
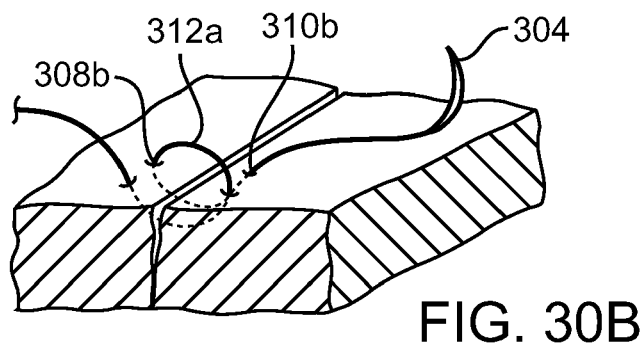
Figure 30C:
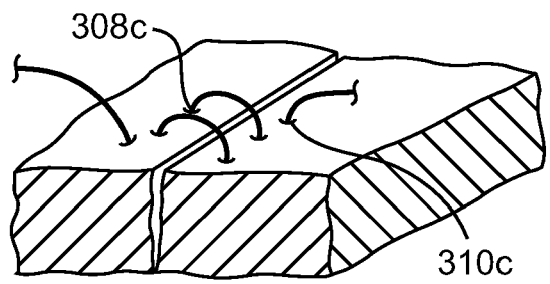
Figure 30D:
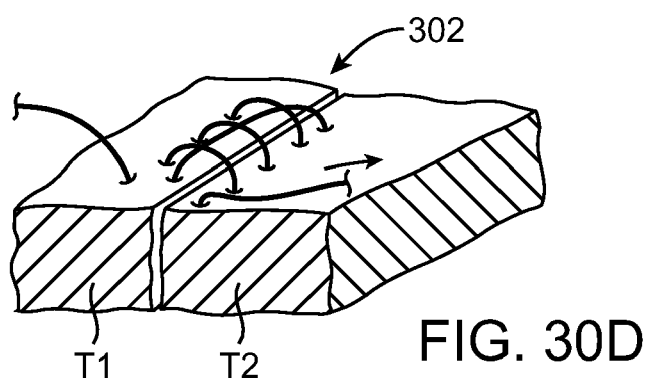

As seen in FIGS. 30A and 30D, a first tissue portion T1 may be affixed to a second tissue portion T2 using a needle 304 and a suture 306 affixed thereto. The needle has a sharpened distal end and suture 306 is affixed to a proximal end of the needle, with the needle and suture typically comprising any of the commercially available surgical structures. The needle is inserted distally through the tissue portions as shown in FIG. 30A, for example, on either side of an incision or the like, with the needle entering the tissue at a first insertion point 308a and exiting the tissue at a first exit point 310a. A first clamp of the suturing device may effect movement of the needle from the proximal end portion during insertion, while a second clamp of the suturing device may grasp and pull the distal end portion while the needle is pulled from the tissue, as explained above. The suturing device or other needle driver will not be shown for simplicity.

As seen in FIG. 30B, a first loop 312a is completed by again passing the needle through the tissue T1, T2, with the needle entering the tissue at a second insertion point 308b and exiting from a second exit point 310b that are near the first insertion point and first exit point, respectively. As seen in FIG. 30C, a second loop 312b is similarly formed using an adjacent third insertion point 308c and third exit point 310c.

Figure 31A:
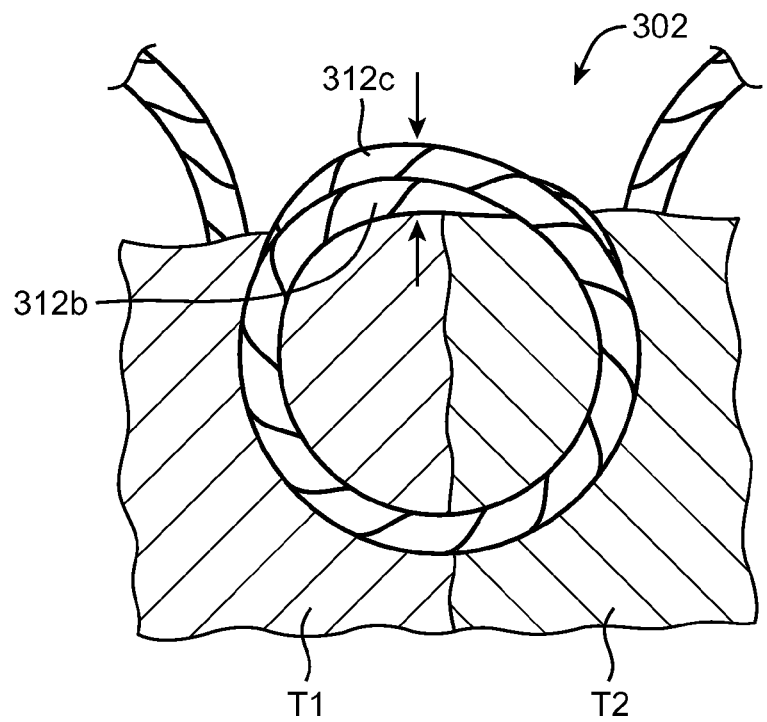
FIGS. 31A and 31B schematically illustrate a suture knot tied according to the method of FIGS. 30A-30D.
Figure 31B:
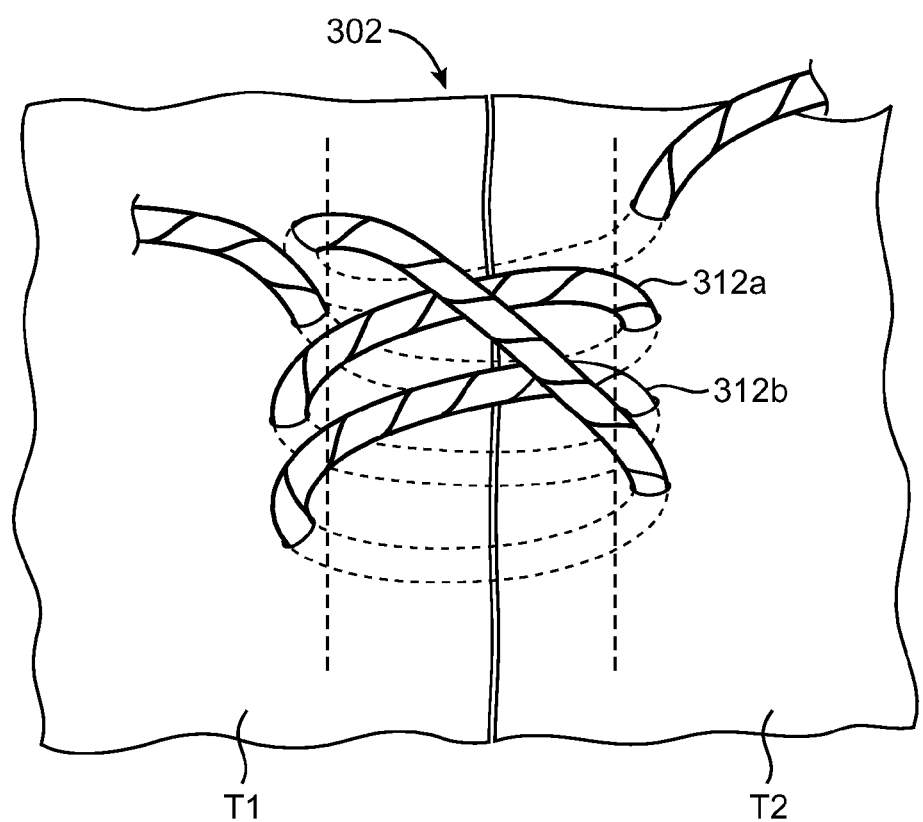

Referring now to FIGS. 30D and 31B, a third loop 312c (with associated fourth entry point 308d and fourth exit point 310d) are formed, with the external portion of the third loop crossing an exposed portion of at least one of the first loop 312a and the second loop 312b. Third loop 312c preferably crosses both first loop 312a and second loop 312b, as shown. Additional loops may be formed before, between, and/or after the first, second, and third loops 312a-312c, and the suture loops may be pulled tight after each is formed or only after more than one is formed.

After forming of the third loop, the needle and/or suture distal of the third loop is pulled sufficiently tight to bring the crossing sutures into firm engagement. The suture tension on the outer third loop presses against the inner first and/or second loop, which is counteracted by the compression of the encircled tissue within the inner loops. This, with the friction between suture and the tissue, can effectively anchor the suture to the tissue and prevent axial movement of the suture when the suture proximal of knot 302 is pulled proximally, and/or when the suture distal of the knot is pulled distally.

Advantageously, knot 302 can be tied using motions similar to those used to form basic stitches, preferably without having to remove a needle driver or grasper such as the suturing devices described herein from the hand of the surgeon, optionally using only one hand of the surgeon (often that holds the suturing device) to completely form the knot. Additionally, deleterious abrasion of the suture (such as that which can occur when other knots are tied away from the tissue and then moved down the suture to the tissue) can be reduced or effectively eliminated.

While exemplary embodiments of the invention have been described in detail, by way of example and for clarity of understanding, a variety of modifications, changes, and adaptations will be obvious to those of skill in the art. For example, along with the exemplary drive linkages described herein, still further drive linkages may be provided, including those making use of cables and pulleys, worm gears, and the like. Hence, the scope of the present invention is limited solely by the appended claims.

What is claimed is:

1. A suturing device for use with a suturing needle by a surgeon having a hand, the device comprising:
   a body having a proximal end and a distal end;
   a first clamp near the distal end of the body;
   a second clamp near the distal end of the body;
   a handle configured for grasping by the hand of the surgeon and actuatable between an open hand configuration and a closed hand configuration by the hand of the surgeon; and
   a linkage coupling the handle with the first and second clamps, the linkage effecting movement of the first and second clamps between a grasping configuration and a displaced configuration, each clamp grasping the needle at an associated grasping location in the grasping configuration and laterally displaced from the needle in the displaced configuration, the grasping locations substantially fixed relative to the body;
   the linkage, in response to movement of the handle between the open handed configuration and the closed handed configuration, driving the first and second clamps between;
      a needle insertion configuration with the first clamp in the grasping configuration along a proximal portion of the needle and the second clamp in the displaced configuration, and
      a needle withdrawal configuration with the second clamp in the grasping configuration along a distal portion of the needle and the first clamp in the displaced configuration;
   wherein the linkage comprises an alternatable drive element, the alternatable drive element alternating between a first configuration and a second configuration in response to movement of the handle between the open hand configuration and the closed hand configuration;
   the alternatable drive element in the first configuration drivingly coupling the handle to a first portion of the linkage and operatively decoupling the handle from a second portion of the linkage so that a movement of the handle between the open hand configuration and the closed hand configuration with the alternatable drive element in the first configuration drives the clamps from the withdrawal configuration to the insertion configuration, and
   the alternatable drive element in the second configuration operatively decoupling the handle from the first portion of the linkage and drivingly coupling the handle to the second portion of the linkage so that the movement of the handle between the open hand configuration and the closed hand configuration with the alternatable drive element in the second configuration drives the clamps from the insertion configuration to the withdrawal configuration;
   such that repeating the movement of the handle alternates the clamps between the insertion configuration and the withdrawal configuration with the grasping locations remaining substantially fixed relative to the body.

2. The suturing device of claim 1, wherein movement of the handle from the closed-hand configuration to the open-hand configuration and back to the closed-hand configuration defines a handle actuation cycle, and wherein support for the needle alternates once between the first clamp and the second clamp during each handle actuation cycle, and wherein the surgeon can insert the needle into tissue by manipulating the handle while the needle is grasped by one of the clamps.

3. The suturing device of claim 2, wherein each clamp opens after the other clamp has closed during the handle actuation cycle so that the clamps maintain the needle at a substantially fixed location relative to the body.

4. The suturing device of claim 1, wherein during actuation the linkage displaces the first clamp laterally from around the needle after the second clamp grasps the needle, and wherein during actuation the linkage displaces the second clamp laterally from around the needle after the first clamp grasps the needle.

5. The suturing device of claim 4, wherein each clamp has a reciprocatable shaft extending proximally from the clamp to the body, wherein the linkage reciprocates the shafts relative to the body during the actuation cycle so as to move each clamp distally, and wherein the linkage thereafter closes the distally extended clamp around the needle.

6. The suturing device of claim 5, wherein at least one associated spring inhibits closing of each clamp before the clamp is adjacent the needle.

7. The suturing device of claim 1, further comprising a release input coupled to the linkage so as to release the needle from the first and second clamps.

8. The suturing device of claim 1, further comprising the needle, wherein the needle comprises an off-the-shelf needle sold primarily for standard open or laparoscopic surgery.

9. The suturing device of claim 1, wherein the clamping locations of the first and second clamps are axially offset along a length of the needle and angularly offset so as to accommodate axial curvature of the needle.

10. The suturing device of claim 1, wherein the handle comprises a proximal handle coupled to the body so as to actuate along a handle actuation plane, wherein the first and second clamps are oriented to support the needle so that an axis of the needle traverses the handle actuation plane.

11. The suturing device of claim 1, wherein the suturing device is composed of chemically sterilizable materials.

12. The suturing device of claim 1, wherein the body extends along an axis from a proximal end to a distal end adjacent the first and second clamps, and wherein the alternatable drive element is driven laterally relative to the axis of the body by the handle actuation cycle between the first configuration and the second configuration, the alternatable drive element movable axially relative to the body axis so as to actuate and displace the driven clamp from about the needle.

13. The suturing device of claim 12, further comprising an alternatable latch movable laterally between a first configuration and a second configuration in response to movement of the alternatable drive element, wherein the alternatable latch in the first configuration inhibits movement of the first clamp, and wherein the alternatable latch in the second configuration inhibits movement of the second clamp, and wherein each clamp has an associated spring, the spring inducing movement of the clamp proximally from the grasping configuration toward the displaced configuration in response to movement of the alternatable latch.

14. The suturing device of claim 1, wherein the body extends from a proximal handle of the body distally toward the first and second clamps, the handle articulatably coupled to the body so that a hand can grasp and move the body while fingers of the hand articulate the handle, and wherein the articulation of the handle effects grasping and releasing of the needle by the clamps.

15. The suturing device of claim 1, wherein an actuation axis extends between each clamp and the body, each clamp comprising a pair of opposed driven surfaces which angle laterally outwardly along the axis, wherein the driven surfaces of each clamp are moved axially by pushing engagement of corresponding driving surfaces of a drive mechanism so that the clamp moves along the axis, and are driven laterally by sliding engagement between the driving surfaces and the driven surfaces so that the clamp opens and closes.

16. The suturing device of claim 1, wherein the first and second clamps are alternatingly latched by an alternatable latch, and further comprising moving the alternatable latch laterally between a first configuration and a second configuration in response to the handle actuation cycle, wherein the alternatable latch in the first configuration inhibits movement of the first clamp, and wherein the alternatable latch in the second configuration inhibits movement of the second clamp.

17. The suturing device of claim 1, wherein the suturing device is configured for manually grasping and manipulation of the body with the hand of the surgeon, wherein the body comprises a rigid grasping base, and wherein the clamps are operatively coupled to the handle so that grasping and releasing of the needle can be effected by articulating the handle with fingers of the hand while the hand grasps the grasping base of the body.

18. The suturing device of claim 1, wherein the clamps accommodate a range of oblique angles between the needle and a shaft of the clamp for proximal or distal suturing, and wherein cycling of the linkage substantially maintains the oblique angle.

19. The suturing device of claim 1, further comprising a detachable coupler releasably coupling the first and second clamps to the body, the first and second clamps being disposable, and third and fourth disposable clamps for releasably coupling to the body in place of the first and second clamps so that each clamp can be used to suture tissue of only a single patient.

20. The suturing device of claim 1, wherein repeated cycling of the linkage effects grasping of the needle with each clamp by:
extending the clamp slightly beyond the grasping location of the grasping configuration;
closing the extended clamp on the needle; and
withdrawing the needle with the extended clamp to the grasping location;
so that gradual displacement of the needle relative to the body during repeated cycling of the linkage is inhibited.

21. A suturing device for use with a suturing needle, the device comprising:
a body having a proximal end and a distal end;
a handle disposed near the proximal end of the body, the handle actuatable from a first configuration to a second configuration and back to the first configuration so as to define an actuation cycle;
a linkage;
a first clamp and a second clamp disposed near the distal end of the body, the first and second clamps coupled to the handle by the linkage so that:
a first actuation cycle, initiated while the first clamp is grasping the needle, effects:
advancing of the second clamp toward the needle and grasping of the needle with the second clamp, a second spring being coupled to the second clamp so that advancing of the second clamp imposes a load on the second spring, and
after grasping of the needle with the second clamp, decoupling the first clamp from a portion of the linkage, release of the needle from the first clamp and retraction, by a first spring, of the first clamp away from the needle; and
a second actuation cycle, initiated while the second clamp is grasping the needle, effects:
advancing of the first clamp toward the needle and grasping of the needle with the first clamp, the first spring being coupled to the first clamp so that advancing of the first clamp imposes a load on the first spring, and
after grasping of the needle with the first clamp, decoupling the second clamp from the portion of the linkage, release of the needle from the second clamp and retraction, by the second spring, of the second clamp away from the needle, wherein the clamps substantially inhibit movement of the needle relative to the body throughout the first and second actuation cycles.

22. A suturing device for use with a suturing needle, the device comprising:
a body having a proximal end and a distal end;
a first clamp near the distal end of the body;
a second clamp near the distal end of the body;
a linkage effecting movement of the first and second clamps between a grasping configuration and a displaced configuration, each clamp grasping the needle at an associated grasping location in the grasping configuration and laterally displaced from the needle in the displaced configuration, the grasping locations substantially fixed relative to the body;
wherein repeated cycling of the linkage effects grasping of the needle with each clamp by:
extending the clamp slightly beyond the grasping location of the grasping configuration;
closing the extended clamp on the needle; and
withdrawing the needle with the extended clamp to the grasping location;
so that gradual displacement of the needle relative to the body during the repeated cycling of the linkage is inhibited.

* * * * *